United States Patent
Cogan et al.

(10) Patent No.: US 7,485,657 B2
(45) Date of Patent: *Feb. 3, 2009

(54) ANTI-CYTOKINE HETEROCYCLIC COMPOUNDS

(75) Inventors: Derek Cogan, Sandy Hook, CT (US); Ming-Hong Hao, Ridgefield, CT (US); Alan David Swinamer, Bethel, CT (US); Ronald A. Aungst, Clifton Park, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 498 days.

This patent is subject to a terminal disclaimer.

(21) Appl. No.: 11/120,735

(22) Filed: May 3, 2005

(65) Prior Publication Data

US 2005/0256113 A1    Nov. 17, 2005

Related U.S. Application Data

(60) Provisional application No. 60/570,284, filed on May 12, 2004.

(51) Int. Cl.
*A61K 31/415* (2006.01)
*C07D 233/00* (2006.01)

(52) U.S. Cl. .................... 514/385; 514/403; 548/300.1; 548/373.1

(58) Field of Classification Search .................. 514/385, 514/403; 548/300.1, 373.1
See application file for complete search history.

(56) References Cited

U.S. PATENT DOCUMENTS

| | | | |
|---|---|---|---|
| 5,723,483 A | 3/1998 | Labeeuw et al. | |
| 6,080,763 A | 6/2000 | Regan et al. | |
| 7,166,628 B2 * | 1/2007 | Cogan et al. | 514/383 |
| 2005/0004176 A1 | 1/2005 | Dyckman et al. | |
| 2005/0153972 A1 | 7/2005 | Cogan et al. | |

FOREIGN PATENT DOCUMENTS

| | | |
|---|---|---|
| DE | 43 02 051 A1 | 7/1994 |
| DE | 4302051 A1 | 7/1994 |
| WO | WO 96/32382 | 10/1996 |
| WO | WO 96/32382 A1 | 10/1996 |
| WO | WO 99/51580 | 10/1999 |
| WO | WO 99/51580 A1 | 10/1999 |
| WO | WO 00/24735 | 5/2000 |
| WO | WO 00/24735 A1 | 5/2000 |
| WO | WO 01/72740 A1 | 10/2001 |
| WO | WO 03/002910 A1 | 1/2003 |
| WO | WO 03/022820 A1 | 3/2003 |
| WO | WO/03022820 A1 | 3/2003 |
| WO | WO 03/030902 A1 | 4/2003 |
| WO | WO/03030902 A1 | 4/2003 |
| WO | WO 03/063781 A2 | 8/2003 |
| WO | WO/03063781 A2 | 8/2003 |
| WO | WO 2004/050642 A1 | 6/2004 |
| WO | WO 2005/009973 A1 | 2/2005 |
| WO | PCT/US2005/015601 | 5/2005 |

OTHER PUBLICATIONS

Copending U.S. Appl. Nos. 11/002,022 and 11/470,849.*
Liverton et al., J. Med. Chem., 1999, 42, 2180-2190, especially p. 2180 and 2185.*
Moreland et al, The New England Journal of Medicine, vol. 337, No. 3, pp. 141-147, 1997.*
English Translation for DE 43 02 051 A1

* cited by examiner

*Primary Examiner*—Rei-Tsang Shiao
*Assistant Examiner*—Susannah Chung
(74) *Attorney, Agent, or Firm*—Michael P. Morris; Mary-Ellen M. Devlin; Anthony P. Bottino

(57) ABSTRACT

Disclosed are compounds of formula (I)

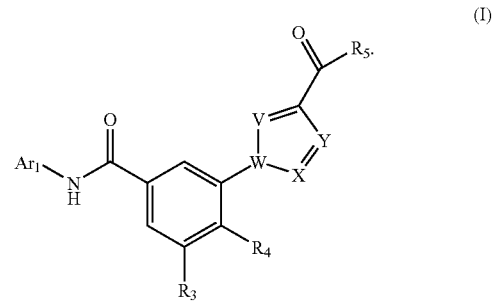

The compounds inhibit production of cytokines involved in inflammatory processes and are thus useful for treating diseases and pathological conditions involving inflammation such as chronic inflammatory disease. Also disclosed are processes for preparing these compounds and the pharmaceutical compositions comprising these compounds.

11 Claims, No Drawings

ANTI-CYTOKINE HETEROCYCLIC COMPOUNDS

APPLICATION DATA

This application claims benefit to U.S. provisional application No. 60/570,284 filed May 12, 2004.

TECHNICAL FIELD

This invention relates to compounds of formula (I)

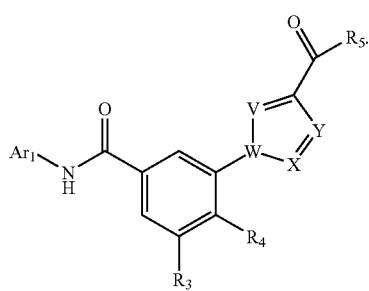

The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND INFORMATION

Tumor necrosis factor (TNF) and interleukin-1 (IL-1) are important biological entities collectively referred to as proinflammatory cytokines which play a role in cytokine mediated diseases. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28-38). Studies suggest that inflammatory changes mediated by cytokines may be involved in endothelial cell pathogenesis including restenosis after percutaneous transluminal coronary angioplasty (PTCA) (Tashiro, H., et al., 2001 March, *Coron Artery Dis* 12(2):107-13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24-5, 1997). These include the treatment of rheumatoid arthritis, Crohn's disease and ulcerative colitis (Rankin, E. C. C., et al., 1997, *British J. Rheum.* 35: 334-342 and Stack, W. A., et al., 1997, *Lancet* 349: 521-524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A,* 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines has been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.*, 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J*, 15, 281). Circulating TNFα may also contribute to weight loss associated with this disease (N. Takabatake et al., 2000, *Amer. J Resp. & Crit. Care Med.*, 161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol.*, 278, L3-12), kidney (Lemay et al., 2000, *Transplantation*, 69, 959), and the nervous system (Mitsui et al., 1999, *Brain Res.*, 844, 192).

TNFα is also a potent osteoclastogenic agent and is involved in bone resorption and diseases involving bone resorption (Abu-Amer et al., 2000, *J. Biol. Chem.*, 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.,* 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and post-menopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 Suppl 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke. TNFα anatagonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production, see J Surg Res 2000 May 15 90(2)95-101; Shock Sep. 10, 1998(3):160-75. p 38MAP kinase pathway plays an role in B.burgdorferi-elicited infammation and may be useful in treating inflammation induced by the Lyme disease agent. Anguita, J. et. al., *The Journal of Immunology*, 2002, 168:6352-6357.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

Compounds active against p38 MAP kinase can also be useful for treating various types of cancers as described in WO 03/068223.

U.S. Pat. No. 5,162,360 discloses N-substituted aryl-N'-heterocyclic substituted urea compounds which are described as being useful for treating hypercholesterolemia and atherosclerosis. Di-substituted aryl and heteroaryl compounds are also disclosed in U.S. Pat. Nos. 6,080,763; 6,319,921; 6,297,381 and 6,358,945. The compounds in the patents are alleged to possess anti-cytokine activity and are therefore useful in treating diseases associated with inflammation.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

The work cited above supports the principle that inhibition of cytokine production with small molecule compounds will be beneficial in the treatment of various disease states.

It is therefore an object of the invention to provide compounds of formula (I)

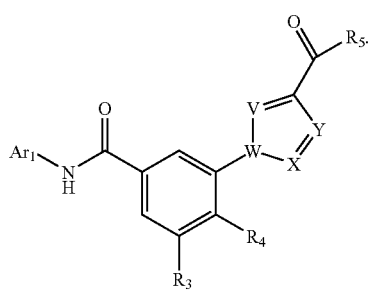

It is a further object of the invention to provide methods for treating cytokine mediated diseases and pathological conditions involving inflammation such as chronic inflammatory disease, using the novel compounds of the invention.

It is yet a further object of the invention to provide pharmaceutical compositions and processes of preparation of the above-mentioned novel compounds.

DETAILED DESCRIPTION OF THE INVENTION

In the broadest generic embodiment, there is provided compounds of the formula (I)

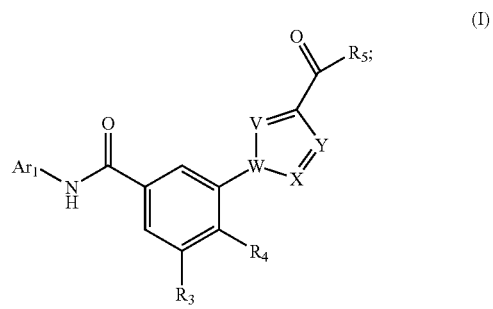

wherein:

the

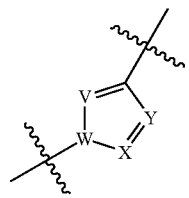

cyclic moiety is

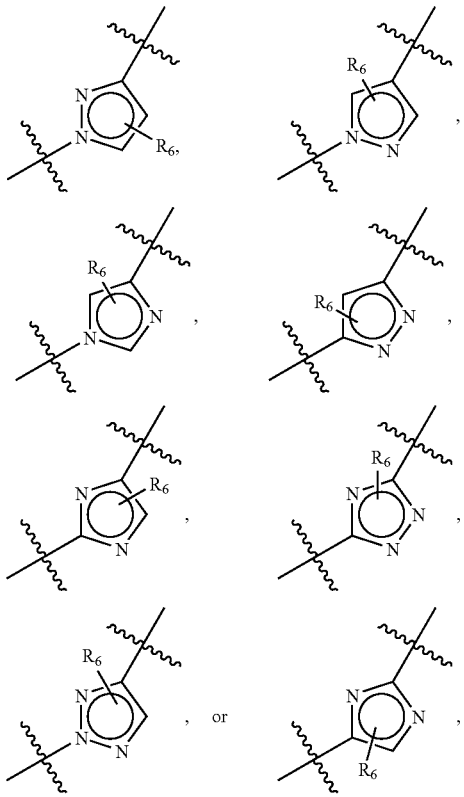

where $R_6$ can be covalently attached to any position on the ring where possible.

preferred are

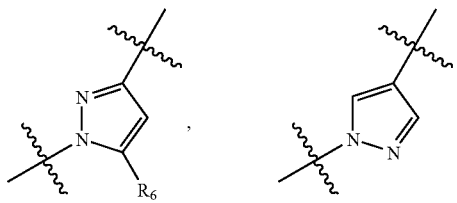

Ar$_1$ is chosen from (i), (ii) and (iii) below:
i) a carbocycle substituted by R$_1$, R$_2$ and R$_x$,

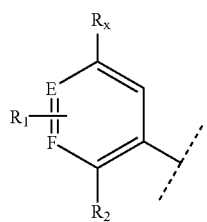

wherein one of E or F is nitrogen and the other is carbon, R$_1$ is covalently attached to either E or F, and when nitrogen is N-R$_1$ the double bond between E and F is not present;

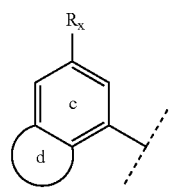

wherein c is a benzo ring fused to ring d which is a 5-7 membered heterocyclic ring optionally substituted by an oxo (=O) group and one to two R groups each independently being hydrogen or C1-3 alkyl;

R$_1$ is chosen from hydrogen, NO$_2$, —N(R$_c$)$_2$, —(CH$_2$)$_n$—C(O)—N(R$_a$)$_2$, —(CH$_2$)$_n$—N(R$_a$)$_2$, J-C(O)—N(R$_c$)—, J-S(O)$_m$—N(R$_c$)—, C1-6 alkylS(O)$_m$— or R$_1$ is chosen from C1-6 alkyl, C3-7 cylcoalkyl, C1-5 alkoxy or C3-7 cycloalkoxy, C1-5 alkylthiol or C3-7 cycloalkylthiol, C1-5 acyl, C1-5 alkoxycarbonyl, C1-5 acyloxy, C1-5 acylamino, C2-5 alkenyl, C2-5 alkynyl, heterocycle, heterocycleC1-6 alkyl, heteroaryl, heteroarylC1-6 alkyl and nitrile; each of the aforementioned where possible are optionally partially or fully halogenated or are optionally further substituted with alkylsulfonylamino, aminocarboxyl, alkoxyl, amino, alkylamino, dialkylamino, hydroxyl, oxo, nitro or nitrile;

J is chosen from C1-10 alkyl and carbocycle each optionally substituted by R$_b$;

R$_2$ is chosen from:
hydrogen, halogen, nitrile, C1-5 alkylS(O)$_m$—, arylS(O)$_m$, J-O—C(O)—O—, N(R$_c$)$_2$—C(O)—(CH$_2$)$_n$—, C1-6 acetyl, aroyl, C1-6alkoxycarbonyl, C1-6 alkyl, C3-7cycloalkyl, C1-6 alkoxy, C3-5cycloalkoxy, C1-5 alkylC1-5 alkoxy, hydroxy, hydroxy C1-5 alkyl, and amino optionally mono- or di-substituted by C1-5 alkyl, aryl or aryl C1-5 alkyl; each of the aforementioned where possible are optionally partially or fully halogenated or are optionally further substituted with C1-3 alkyl, alkylsulfonylamino, alkoxyl, amino, alkylamino, dialkylamino, hydroxyl, oxo, nitro or nitrile;

each R$_x$ is chosen from C1-6 alkyl or C3-7 cycloalkyl each being optionally substituted by C1-3 alkyl and optionally partially or fully halogenated, C1-4 acyl, aroyl, C1-4 alkoxy, C1-5alkylS(O)$_m$—, each may optionally be partially or fully halogenated, halogen, C1-6 alkoxycarbonyl, carbocyclesulfonyl;

each R$_c$ is independently hydrogen or C1-5 alkyl;

R$_3$, R$_4$, R$_6$, R$_7$ and R$_8$ are each independently chosen from hydrogen, halogen, C1-5 alkyl, C1-5 alkoxy, C1-5 alkylC1-5 alkoxy, hydroxy, hydroxy C1-5 alkyl or amino optionally mono- or di-substituted by C1-5 alkyl, aryl or aryl C1-5 alkyl;

R$_5$ is:
R$_a$, —O—R$_a$, —S—R$_a$, —N(R$_a$)$_2$, —C(O)—R$_a$, —NH(CR$_7$R$_8$)$_n$—R$_a$, —(CR$_7$R$_8$)$_n$—N(R$_a$)$_2$, —(CR$_7$R$_8$)$_n$—R$_a$, —O(CR$_7$R$_8$)$_n$—R$_a$, —C(O)—O(CR$_7$R$_8$)$_n$—R$_a$, —C(O)(CR$_7$R$_8$)$_n$—R$_a$ and —C(O)NH(CR$_7$R$_8$)$_n$—;

or R$_5$ is a ring system chosen from aryl, heteroaryl or heterocyclyl each optionally substituted by R$_a$;

R$_a$ and R$_b$ are each independently chosen from hydrogen, C1-5 alkyl, hydroxyC1-5 alkyl, C2-5 alkenyl, C2-5 alkynyl, carbocycle, heterocycle, heteroaryl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, each of the aforementioned are optionally partially or fully halogenated, or R$_a$ and R$_b$ are chosen from C1-5 alkylsulphonylamino, hydroxy, oxo, halogen, nitro and nitrile, wherein each carbocycle, heterocycle or heteroaryl for R$_a$ and R$_b$ is optionally substituted by amino, C1-3 alkyl, halogen or hydroxy;

n is 1-5;
m is 0, 1 or 2;

and

X is O or S or the pharmaceutically acceptable salts, acids, esters or isomers thereof.

In another embodiment, there are provided compounds of the formula (I) as described above and wherein J is chosen from C1-10 alkyl, aryl and C3-7 cycloalkyl each optionally substituted by R$_b$;

R$_2$ is independently chosen from hydrogen, J-O—C(O)—O—, C1-6 alkoxy, C1-6 alkyl, C1-6 acetyl, aroyl, halogen, methoxycarbonyl, phenylsulfonyl, C1-5 alkylS(O)$_m$— and C3-7 cycloalkyl optionally substituted by C1-3 alkyl, each R$_2$ where possible may be optionally partially or fully halogenated;

$R_1$ is chosen from hydrogen, C1-6 alkyl, C1-5 alkylS$(O)_m$—, J-S$(O)_m$—N($R_c$)—, C1-5 alkoxy, C1-5 alkylthiol, $NH_2$—C(O)—$(CH_2)_n$—, $(R_c)_2$N C1-6 alkyl, C1-5acylNH—, —$NH_2$, —$NO_2$, heteroaryl chosen from pyrazole, triazole, imidazole and tetrazole, and nitrile;

ring d is a 5-6 membered heterocyclic ring such that rings c and d fuse to form the following:

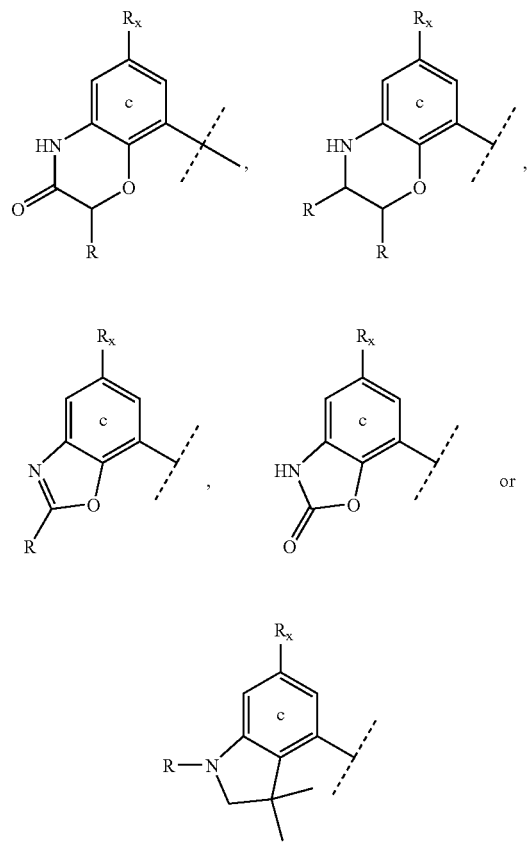

where each R is independently hydrogen or C1-3 alkyl;

$R_3$ and $R_4$ are each independently chosen from hydrogen, C1-3 alkoxy, C1-3 alkyl and halogen;

n is 1-4;

$R_a$ and $R_b$ are each independently chosen from hydrogen, C1-5 alkyl, C2-5 alkenyl, C2-5 alkynyl, C3-8 cycloalkylC0-2 alkyl, aryl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, C1-5 sulphonylamino, hydroxy, halogen, $CF_3$, $CH_2$—$CF_3$, nitro, nitrile or $R_a$ and $R_b$ are chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone and heteroaryl chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl; wherein each aryl, heterocycle or heteroaryl for $R_a$ and $R_b$ is optionally substituted by amino, C1-3 alkyl, halogen or hydroxyl;

and X is O.

In yet another embodiment, there are provided compounds of the formula (I) as described immediately above and wherein $R_5$ is:

$R_a$, —O—$R_a$, —S—$R_a$, —N$(R_a)_2$, —C(O)—$R_a$, —NH$(CR_7R_8)_n$—$R_a$, —$(CR_7R_8)_n$—N$(R_a)_2$, —$(CR_7R_8)_n$—$R_a$, —O$(CR_7R_8)_n$—$R_a$, —C(O)—O$(CR_7R_8)_n$—$R_a$, —C(O)$(CR_7R_8)_n$—$R_a$ and —C(O)NH$(CR_7R_8)_n$—, wherein n is 1-3;

$R_7$ and $R_8$ are each independently chosen from hydrogen, halogen, C1-5 alkyl, C1-5 alkoxy, C1-5 alkylC1-5 alkoxy, hydroxy, hydroxy C1-5 alkyl or amino optionally mono- or di-substituted by C1-5 alkyl, phenyl or phenylC1-5 alkyl.

In yet another embodiment, there are provided compounds of the formula (I) as described immediately above and wherein $Ar_1$ is:

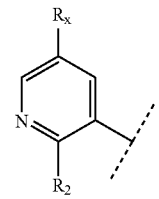

or $Ar_1$ is cyclobutyl, phenyl, naphthyl, tetrahydronaphthyl, indanyl and indenyl each substituted with one $R_1$, one $R_x$, and one $R_2$ group;

$R_1$ is hydrogen, nitrile, $NO_2$, $NH_2$, C1-3acylNH—,

J-S$(O)_m$—N$(R_c)$— where J is C1-10 alkyl, or $R_1$ is

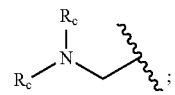

$R_2$ is independently chosen from C1-6 alkyl, C1-6 alkylS$(O)_m$—, C1-3 alkoxy and C3-6 cycloalkyl optionally substituted by C1-3 alkyl, each may optionally be partially or fully halogenated;

$R_3$ and $R_4$ are each independently chosen from hydrogen, C1-3 alkyl, fluoro and chloro;

R6 is chosen from hydrogen and amino;

n is 1-2;

$R_a$ and $R_b$ are each independently chosen from hydrogen, C1-5 alkyl, C3-7 cycloalkylC0-2 alkyl, aryl, C1-5 alkoxy, amino, C1-5 alkylamino, C1-5 dialkylamino, C1-3 acyl, C1-5 alkoxycarbonyl, C1-3 acyloxy, C1-3 acylamino, C1-3 sulphonylamino, hydroxy, halogen, $CF_3$, $CH_2$—$CF_3$, nitro, nitrile;

or $R_a$ is chosen from pyrrolidinyl, pyrrolinyl, morpholinyl, thiomorpholinyl, thiomorpholinyl sulfoxide, thiomorpholinyl sulfone, piperidinyl, piperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl ; wherein each aryl, heterocycle or heteroaryl for $R_a$ and $R_b$ is optionally substituted by amino, C1-3 alkyl, halogen or hydroxyl.

In yet still another embodiment, there are provided compounds of the formula (I) as described immediately above and wherein $Ar_1$ is

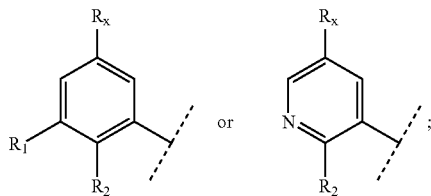

$R_1$ is:
hydrogen, J-S(O)$_2$—NH—, where J is C1-5 alkyl,
or $R_1$ is nitrile, $NO_2$, $NH_2$ or C1-3acylNH—;
wherein $R_x$=$R_2$ each are independently chosen from C1-5 alkyl, C1-5 alkylS(O)$_m$—, C1-4 alkoxy and and C3-5 cycloalkyl optionally substituted by C1-2 alkyl, each may optionally be partially or fully halogenated;

In yet another embodiment, there are provided compounds of the formula (I) as described immediately above and wherein $R_a$ is chosen from hydrogen, C1-5 alkyl, C3-6 cycloalkylC0-2 alkyl, phenyl, C1-5 alkoxy, amino, C1-5 alkylamino, C1-5 dialkylamino, C1-3 acyl, C1-5 alkoxycarbonyl, C1-3 acyloxy, C1-3 acylamino, hydroxy, halogen;

or $R_a$ is chosen from morpholinyl, thiomorpholinyl, thiomorpholinyl sulfoxide, thiomorpholinyl sulfone, piperidinyl, piperidinonyl, pyridinyl, pyrimidinyl, pyrazinyl and pyridazinyl wherein each are optionally substituted by amino, C1-3 alkyl, halogen or hydroxyl.

In yet another embodiment, there are provided compounds of the formula (I) as described immediately above and wherein $R_a$ is chosen from hydrogen, C1-5 alkyl, C3-6 cycloalkyl, phenyl, C1-5 alkoxy, C1-5 alkoxycarbonyl, C1-3 acyloxy, C1-3 acylamino, amino, mono-or-di-C1-4 alkyl amino, hydroxy, halogen;

or $R_a$ is chosen morpholinyl, piperidinyl and pyridinyl wherein each are optionally substituted by amino, C1-3 alkyl, halogen or hydroxyl.

In yet another embodiment, there are provided compounds of the formula (I) as described immediately above and wherein $Ar_1$ is

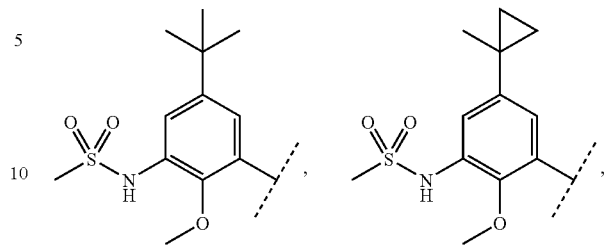

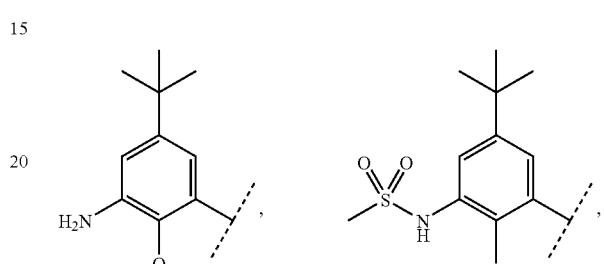

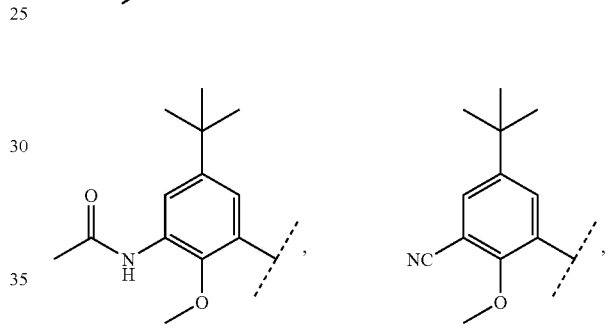

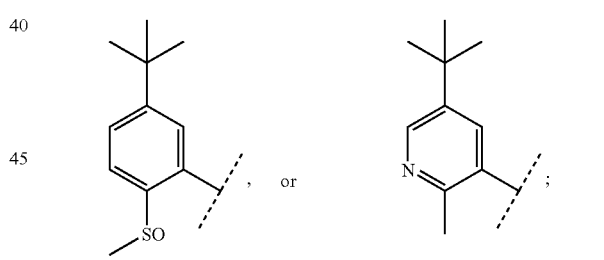

$R_5$ is:
C1-4 alkyl, C3-6 cycloalkyl, morpholinyl($CH_2$)$_{1-2}$—, halogen, C1-3 alkoxy, hydroxy, —N($R_a$)$_2$, —$CF_3$, —$CH_2$—$CF_3$, piperidinyl, phenyl, phenyl —S(O)$_m$— or benzyl each phenyl, heteroaryl or heterocyclic group is optionally substituted by C1-3 alkyl, halogen or hydroxy, or $R_5$ is —NH($CR_7R_8$)$_n$—$R_a$ or —($CR_7R_8$)$_n$—N($R_8$)$_2$ wherein $R_a$ is chosen from hydrogen, phenyl, morpholinyl, piperidinyl, pyridinyl, amino, mono-or-di-C1-3 alkyl amino, cyclopropyl, cyclopentyl, cyclohexyl, C1-5 alkyl and C1-3 alkoxy.

The following are representative compounds of the invention which can be made according to the general schemes and working examples below:

TABLE I

| Structure | Name |
|---|---|
| 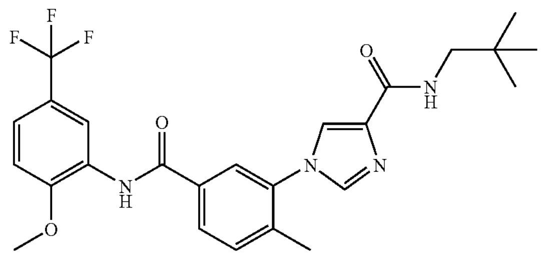 | 1-[5-(2-Methoxy-5-trifluoromethyl-phenylcarbamoyl)-2-methyl-phenyl]-1H-imidazole-4-carboxylic acid (2,2-dimethyl-propyl)-amide |
| 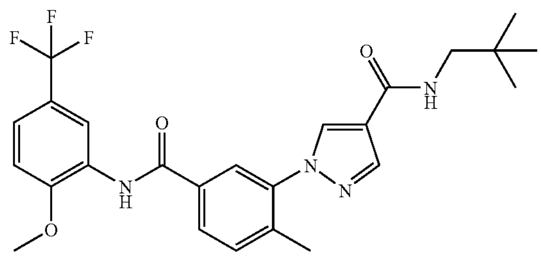 | 1-[5-(2-Methoxy-5-trifluoromethyl-phenylcarbamoyl)-2-methyl-phenyl]-1H-pyrazole-4-carboxylic acid (2,2-dimethyl-propyl)-amide |
| 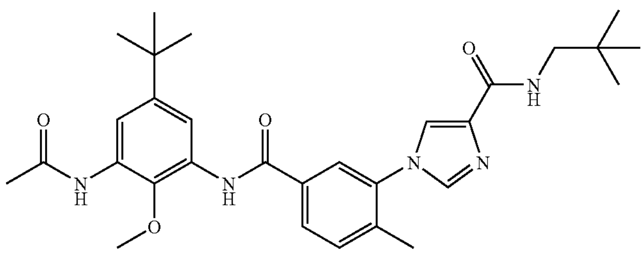 | 1-[5-(3-Acetylamino-5-tert-butyl-2-methoxy-phenylcarbamoyl)-2-methyl-phenyl]-1H-imidazole-4-carboxylic acid (2,2-dimethyl-propyl)-amide |
| 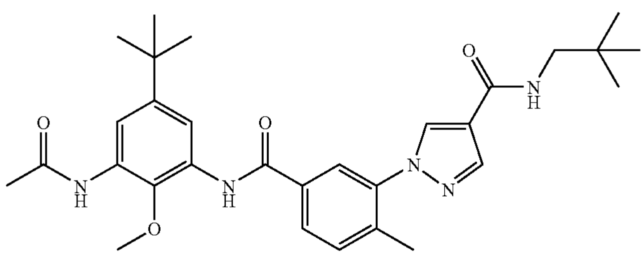 | 1-[5-(3-Acetylamino-5-tert-butyl-2-methoxy-phenylcarbamoyl)-2-methyl-phenyl]-1H-pyrazole-4-carboxylic acid (2,2-dimethyl-propyl)-amide |
| 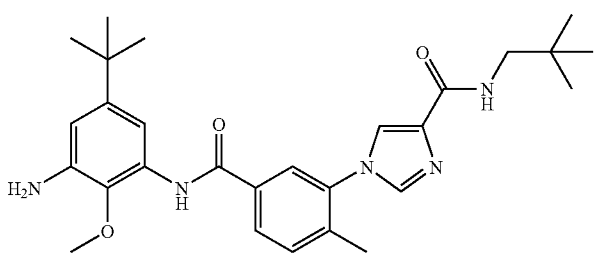 | 1-[5-(3-Amino-5-tert-butyl-2-methoxy-phenylcarbamoyl)-2-methyl-phenyl]-1H-imidazole-4-carboxylic acid (2,2-dimethyl-propyl)-amide |
| 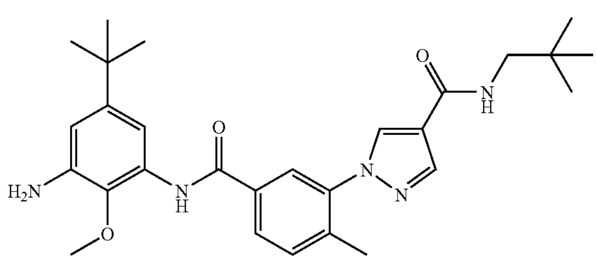 | 1-[-(3-Amino-5-tert-butyl-2-methoxy-phenylcarbamoyl)-2-methyl-phenyl]-1H-pyrazole-4-carboxylic acid (2,2-dimethyl-propyl)-amide |

TABLE I-continued

| Structure | Name |
|---|---|
| 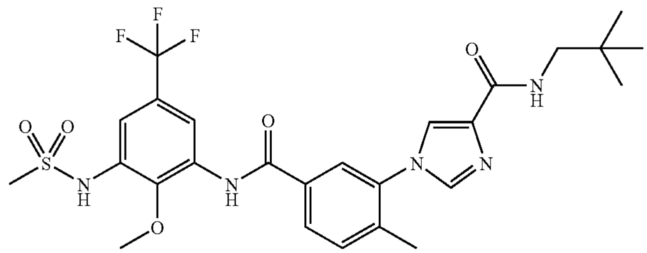 | 1-[5-(3-Methanesulfonylamino-2-methoxy-5-trifluoromethyl-phenylcarbamoyl)-2-methyl-phenyl]-1H-imidazole-4-carboxylic acid (2,2-dimethyl-propyl)-amide |
| 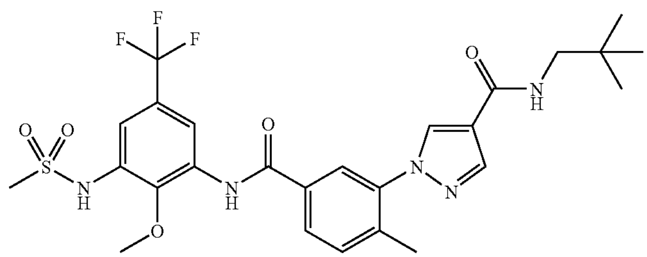 | 1-[5-(3-Methanesulfonylamino-2-methoxy-5-trifluoromethyl-phenylcarbamoyl)-2-methyl-phenyl]-1H-pyrazole-4-carboxylic acid (2,2-dimethyl-propyl)-amide |
| 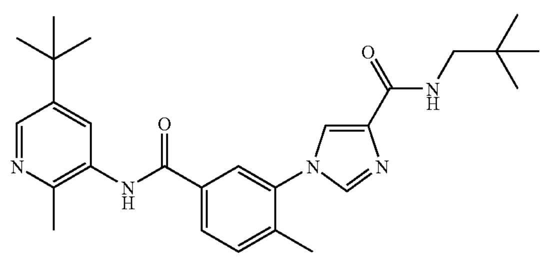 | 1-[5-(5-tert-Butyl-2-methyl-pyridin-3-ylcarbamoyl)-2-methyl-phenyl]-1H-imidazole-4-carboxylic acid (2,2-dimethyl-propyl)-amide |
| 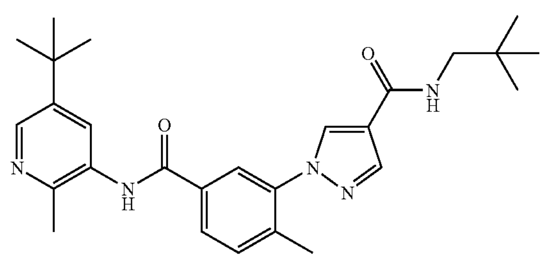 | 1-[5-(5-tert-Butyl-2-methyl-pyridin-3-ylcarbamoyl)-2-methyl-phenyl]-1H-pyrazole-4-carboxylic acid (2,2-dimethyl-propyl)-amide |
| 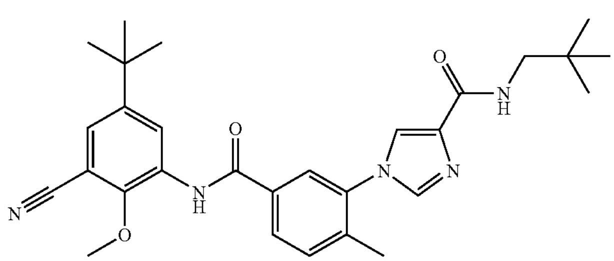 | 1-[5-(5-tert-Butyl-3-cyano-2-methoxy-phenylcarbamoyl)-2-methyl-phenyl]-1H-imidazole-4-carboxylic acid (2,2-dimethyl-propyl)-amide |
| 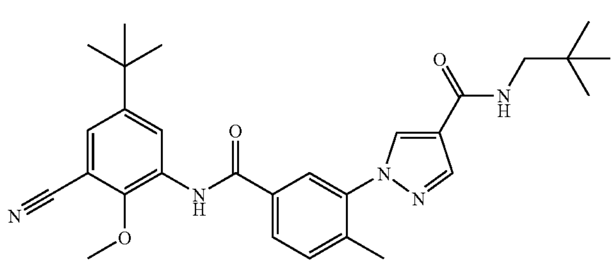 | 1-[5-(5-tert-Butyl-3-cyano-2-methoxy-phenylcarbamoyl)-2-methyl-phenyl]-1H-pyrazole-4-carboxylic acid (2,2-dimethyl-propyl)-amide |

TABLE I-continued

| Structure | Name |
|---|---|
| 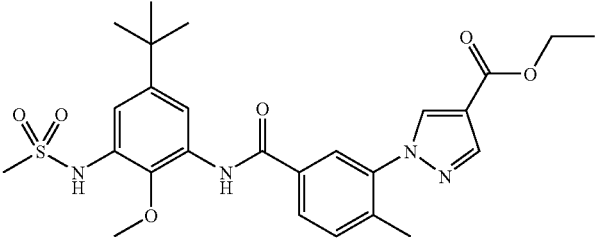 | 1-[5-(5-tert-Butyl-3-methanesulfonylamino-2-methoxy-phenylcarbamoyl)-2-methyl-phenyl]-1H-pyrazole-4-carboxylic acid ethyl ester |
| 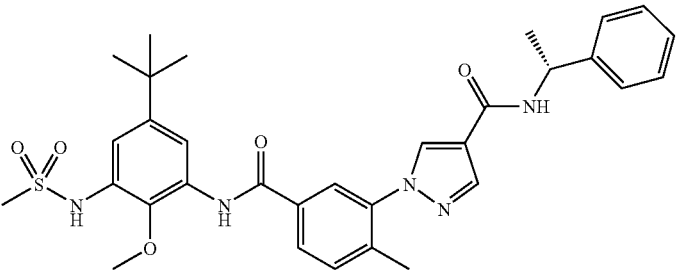 | 1-[5-(5-tert-Butyl-3-methanesulfonylamino-2-methoxy-phenylcarbamoyl)-2-methyl-phenyl]-1H-pyrazole-4-carboxylic acid ((R)-1-phenyl-ethyl)-amide |
| 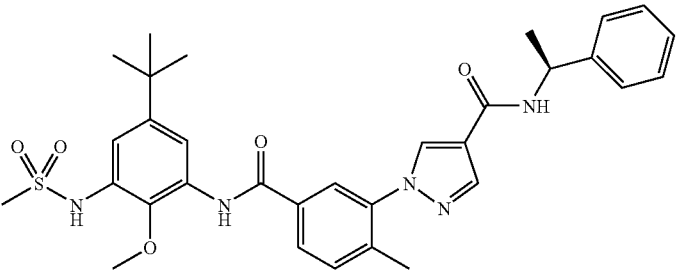 | 1-[5-(5-tert-Butyl-3-methanesulfonylamino-2-methoxy-phenylcarbamoyl)-2-methyl-phenyl]-1H-pyrazole-4-carboxylic acid ((S)-1-phenyl-ethyl)-amide |
| 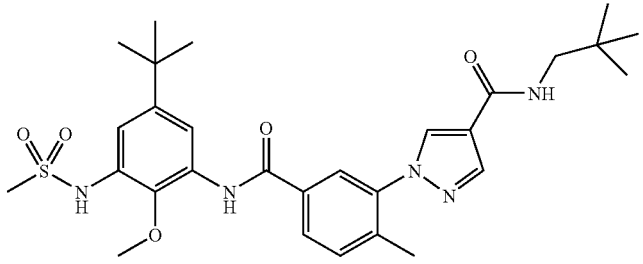 | 1-[5-(5-tert-Butyl-3-methanesulfonylamino-2-methoxy-phenylcarbamoyl)-2-methyl-phenyl]-1H-pyrazole-4-carboxylic acid (2,2-dimethyl-propyl)-amide |
| 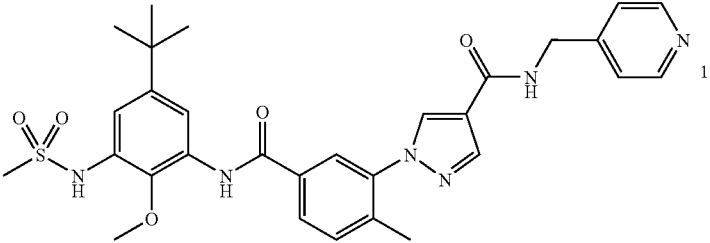 | 1-[5-(5-tert-Butyl-3-methanesulfonylamino-2-methoxy-phenylcarbamoyl)-2-methyl-phenyl]-1H-pyrazole-4-carboxylic acid (pyridin-4-ylmethyl)-amide |

TABLE I-continued

| Structure | Name |
|---|---|
| 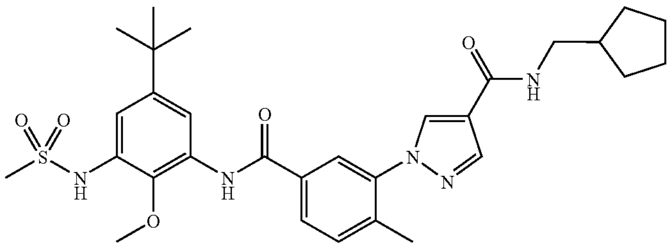 | 1-[5-(5-tert-Butyl-3-methanesulfonylamino-2-methoxy-phenylcarbamoyl)-2-methyl-phenyl]-1H-pyrazole-4-carboxylic acid cyclopentylmethyl-amide |
| 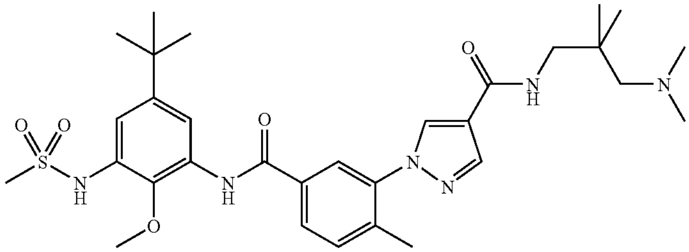 | 1-[5-(5-tert-Butyl-3-methanesulfonylamino-2-methoxy-phenylcarbamoyl)-2-methyl-phenyl]-1H-pyrazole-4-carboxylic acid (3-dimethylamino-2,2-dimethyl-propyl)-amide |
| 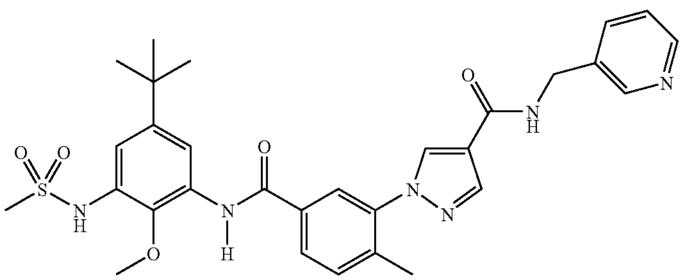 | 1-[5-(5-tert-Butyl-3-methanesulfonylamino-2-methoxy-phenylcarbamoyl)-2-methyl-phenyl]-1H-pyrazole-4-carboxylic acid (pyridin-3-ylmethyl)-amide |
| 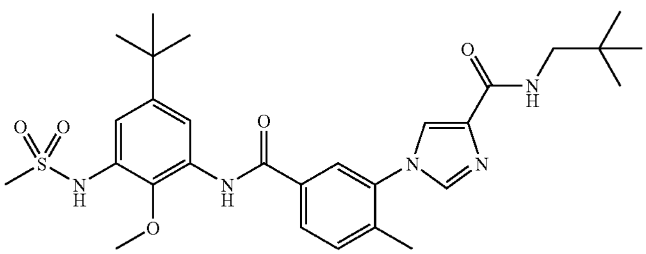 | 1-[5-(5-tert-Butyl-3-methanesulfonylamino-2-methoxy-phenylcarbamoyl)-2-methyl-phenyl]-1H-imidazole-4-carboxylic acid (2,2-dimethyl-propyl)-amide |
| 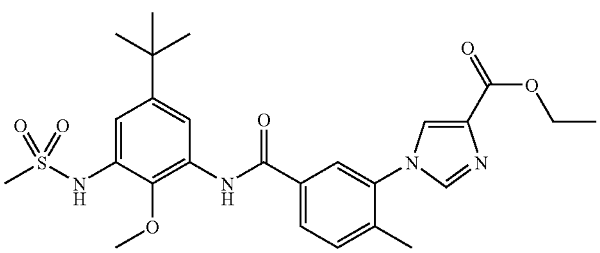 | 1-[5-(5-tert-Butyl-3-methanesulfonylamino-2-methoxy-phenylcarbamoyl)-2-methyl-phenyl]-1H-imidazole-4-carboxylic acid ethyl ester |
| 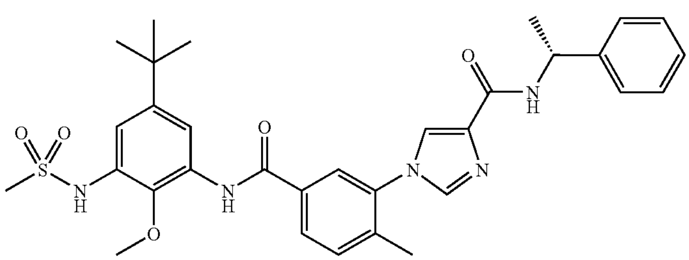 | 1-[5-(5-tert-Butyl-3-methanesulfonylamino-2-methoxy-phenylcarbamoyl)-2-methyl-phenyl]-1H-imidazole-4-carboxylic acid ((R)-1-phenyl-ethyl)-amide |

TABLE I-continued

| Structure | Name |
|---|---|
| 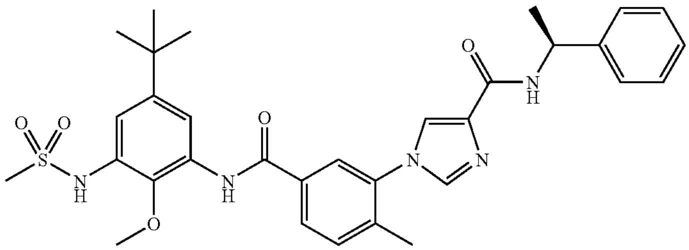 | 1-[5-(5-tert-Butyl-3-methanesulfonylamino-2-methoxy-phenylcarbamoyl)-2-methyl-phenyl]-1H-imidazole-4-carboxylic acid ((S)-1-phenyl-ethyl)-amide |
| 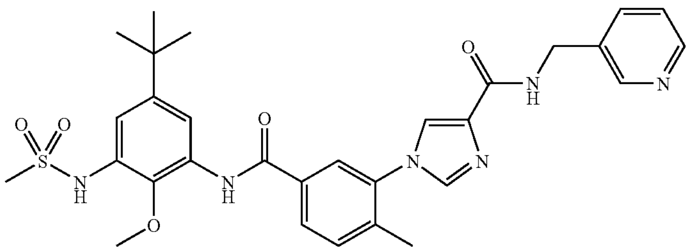 | 1-[5-(5-tert-Butyl-3-methanesulfonylamino-2-methoxy-phenylcarbamoyl)-2-methyl-phenyl]-1H-imidazole-4-carboxylic acid (pyridin-3-ylmethyl)-amide |
| 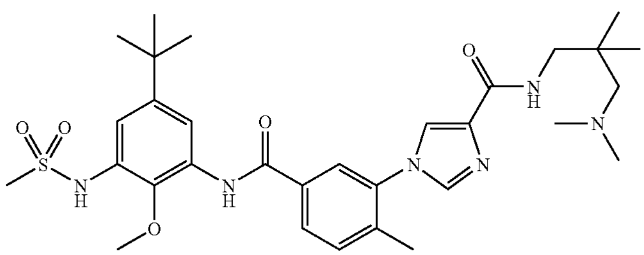 | 1-[5-(5-tert-Butyl-3-methanesulfonylamino-2-methoxy-phenylcarbamoyl)-2-methyl-phenyl]-1H-imidazole-4-carboxylic acid (3-dimethylamino-2,2-dimethyl-propyl)-amide |
| 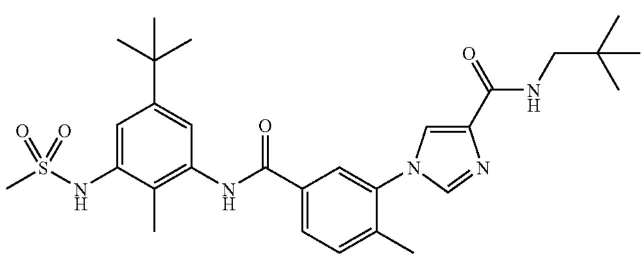 | 1-[5-(5-tert-Butyl-3-methanesulfonylamino-2-methyl-phenylcarbamoyl)-2-methyl-phenyl]-1H-imidazole-4-carboxylic acid (2,2-dimethyl-propyl)-amide |
| 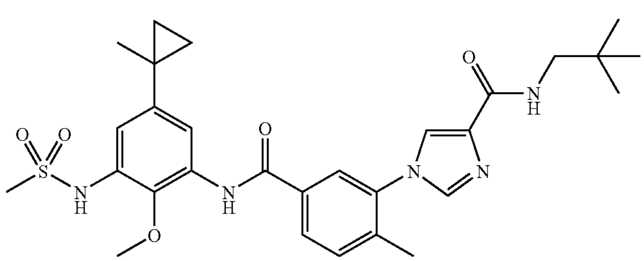 | 1-{5-[3-Methanesulfonylamino-2-methoxy-5-(1-methyl-cyclopropyl)-phenylcarbamoyl]-2-methyl-phenyl}-1H-imidazole-4-carboxylic acid (2,2-dimethyl-propyl)-amide |
| 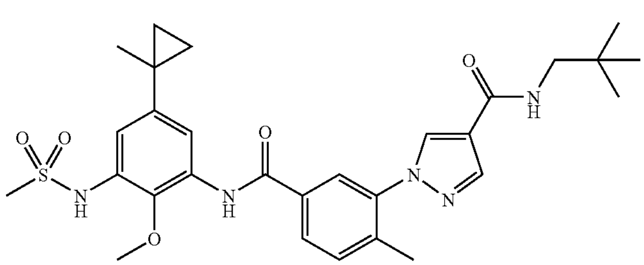 | 1-{5-[3-Methanesulfonylamino-2-methoxy-5-(1-methyl-cyclopropyl)-phenylcarbamoyl]-2-methyl-phenyl}-1H-pyrazole-4-carboxylic acid (2,2-dimethyl-propyl)-amide |

TABLE I-continued

| Structure | Name |
|---|---|
| 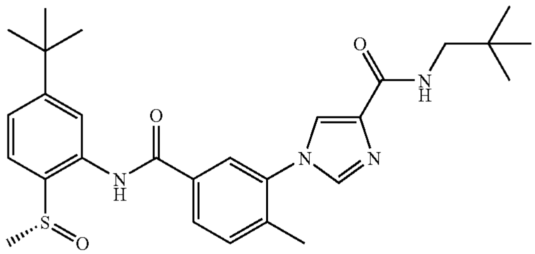 | 1-{5-[5-tert-Butyl-2-((R)-methanesulfinyl)-phenylcarbamoyl]-2-methyl-phenyl}-1H-imidazole-4-carboxylic acid (2,2-dimethyl-propyl)-amide |
| 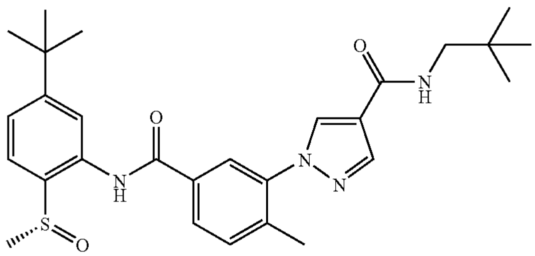 | 1-{5-[5-tert-Butyl-2-((R)-methanesulfinyl)-phenylcarbamoyl]-2-methyl-phenyl}-1H-pyrazole-4-carboxylic acid (2,2-dimethyl-propyl)-amide |
| 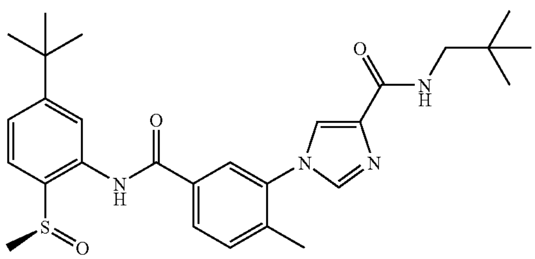 | 1-{5-[5-tert-Butyl-2-((S)-methanesulfinyl)-phenylcarbamoyl]-2-methyl-phenyl}-1H-imidazole-4-carboxylic acid (2,2-dimethyl-propyl)-amide |
| 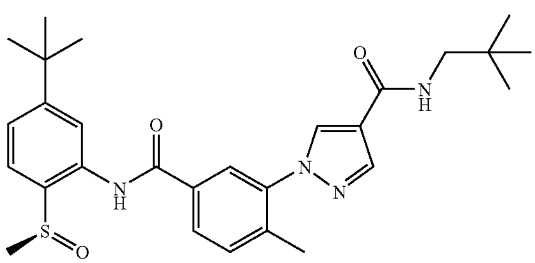 | 1-{5-[5-tert-Butyl-2-((S)-methanesulfinyl)-phenylcarbamoyl]-2-methyl-phenyl}-1H-pyrazole-4-carboxylic acid (2,2-dimethyl-propyl)-amide |
| | 5-Amino-1-[5-(5-tert-butyl-3-methanesulfonylamino-2-methoxy-phenylcarbamoyl)-2-methyl-phenyl]-1H-pyrazole-3-carboxylic acid ethyl ester | or the pharmaceutically acceptable salts, acids, esters or isomers thereof.

In all the compounds disclosed hereinabove in this application, in the event the nomenclature is in conflict with the structure, it shall be understood that the compound is defined by the structure.

Of particular importance according to the invention are compounds of formula (I), for use as pharmaceutical compositions with an anti-cytokine activity.

The invention also relates to the use of a compound of formula (I), for preparing a pharmaceutical composition for the treatment and/or prevention of a cytokine mediated disease or condition.

The invention also relates to pharmaceutical preparations, containing as active substance one or more compounds of formula (I), or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N,O and S. Unless otherwise stated, such heteroaryls include aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical., unless otherwise specified, this shall be understood to include —S(O)—$C_{1-6}$ alkyl and —S(O)$_2$—$C_{1-6}$ alkyl, likewise, —S—$R^a$ may be represented as phenyl —S(O)$_m$— when $R^a$ is phenyl and where m is 0, 1 or 2.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1$-$C_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The invention additionally provides for methods of making the compounds of formula (I). The compounds of the invention may be prepared by the general methods and examples presented below, and methods known to those of ordinary skill in the art. In the schemes below, unless otherwise specified, $Ar_1$, $R_1$-$R_6$ and X in the formulas shown below shall have the meanings defined for these groups in the definition of the formula (I) of the invention, described hereinabove. Intermediates used in the syntheses below are either commercially available or easily prepared by methods known to those skilled in the art. Further reference in this regard may be made to U.S. Pat. No. 6,358,945, U.S. application Ser. Nos. 09/714,539, 09/834,797, 10/120,028, 10/143,322, 10/147,675 and 10/718,380. Each of the aforementioned are incorporated in their entirety.

Reaction progress may be monitored by conventional methods such as thin layer chromatography (TLC). Intermediates and products may be purified by methods known in the art, including column chromatography, HPLC or recrystallization.

Compounds of formula (I) having W=X=N and V=Y=C may be prepared as described in Scheme I. Substituted aniline II is converted to hydrazine derivative III by treatment with $NaNO_2$ to form the diazonium salt, followed by treatment with a suitable reducing agent such as $SnCl_2$. Cyclization with aldehyde IV, as described in a general synthesis of N-1 substituted alkyl 4-pyrazole carboxylates (W. Holzer and G. Seiringer, J. Het. Chem., 1993, 30, 865) provides V ($R_5$=$CO_2H$). Reaction of V with the desired aniline using standard coupling conditions known in the art provides the desired compound of formula (I) or a precursor that can be further modified by methods known in the art to provide the desired compound of formula (I).

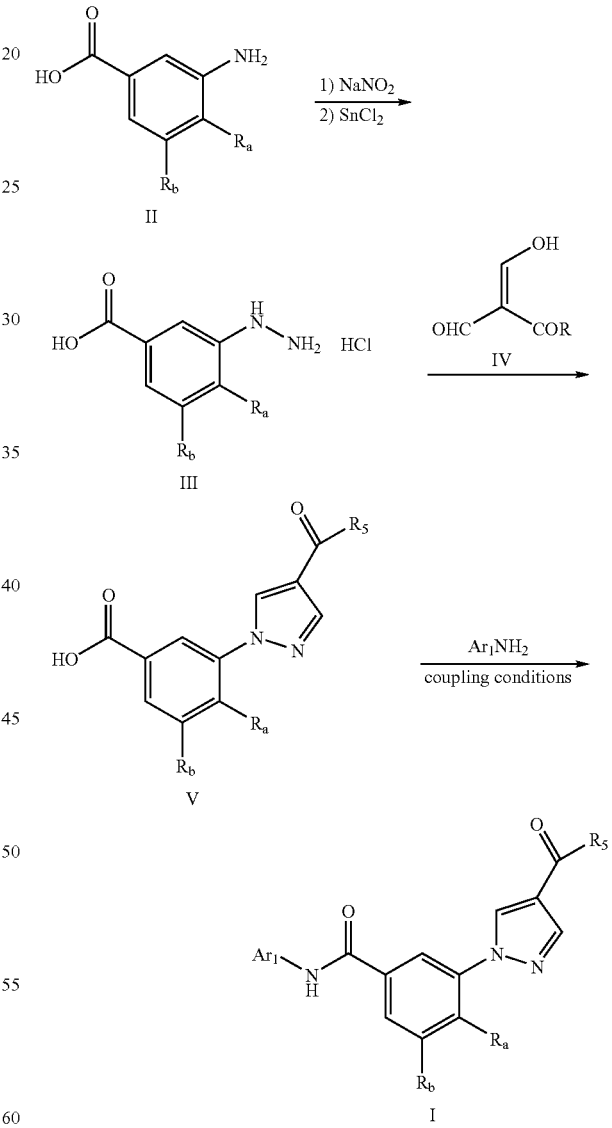

For example, as illustrated in Scheme II, the compound of formula (Ia), having $R_5$=—$OR_a$ may be converted to Ib having $R_5$=—$N(R_a)(R_b)$ by hydrolysis, followed by a coupling of the resulting carboxylic acid as described above with $HN(R_a)(R_b)$.

Scheme II

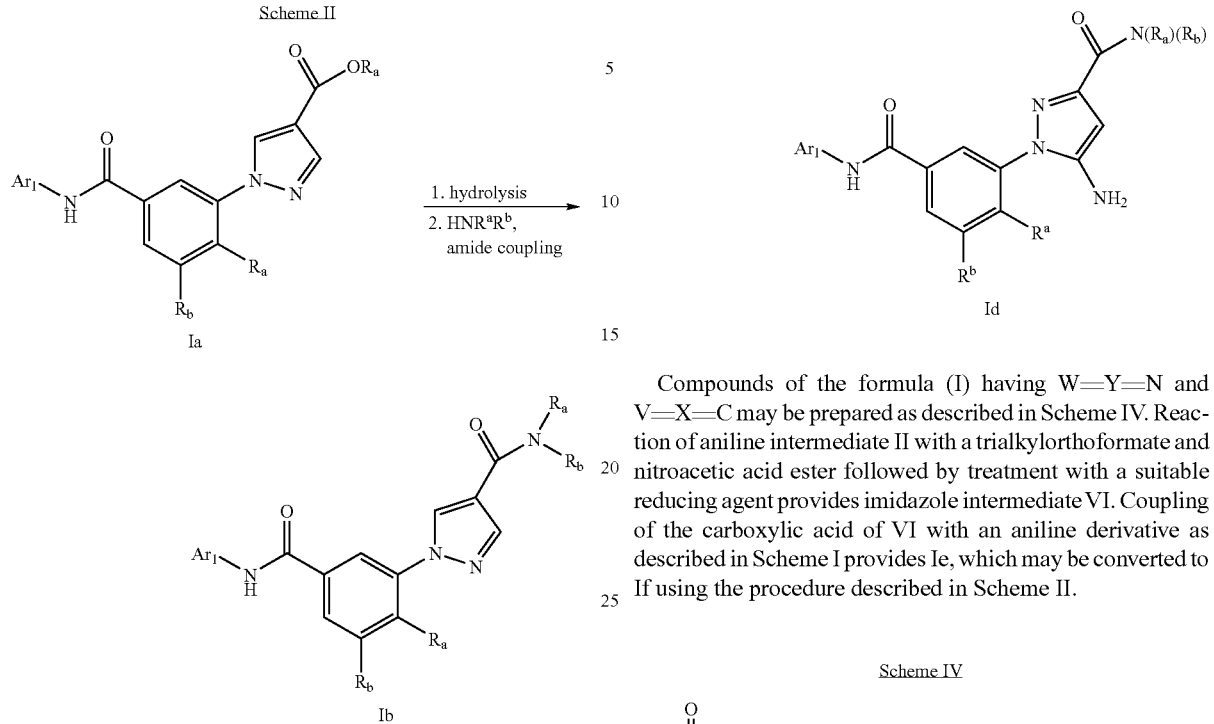

Compounds of formula (I) having V=W=N, X=Y=C and $R_6$=$NH_2$ may be prepared as described in Scheme III. As illustrated below, hydrazine intermediate III is reacted with nitrile VI in the presence of a suitable acid, such as trifluoroacetic acid, to provide the pyrazole of formula (Ic) ($R_5$=$OR_a$, $R_6$=$NH_2$). Further reaction as described in Scheme II provides the compound of formula Id ($R_5$=$N(R_a)(R_b)$, $R_6$=$NH_2$).

Compounds of the formula (I) having W=Y=N and V=X=C may be prepared as described in Scheme IV. Reaction of aniline intermediate II with a trialkylorthoformate and nitroacetic acid ester followed by treatment with a suitable reducing agent provides imidazole intermediate VI. Coupling of the carboxylic acid of VI with an aniline derivative as described in Scheme I provides Ie, which may be converted to If using the procedure described in Scheme II.

Scheme III

Scheme IV

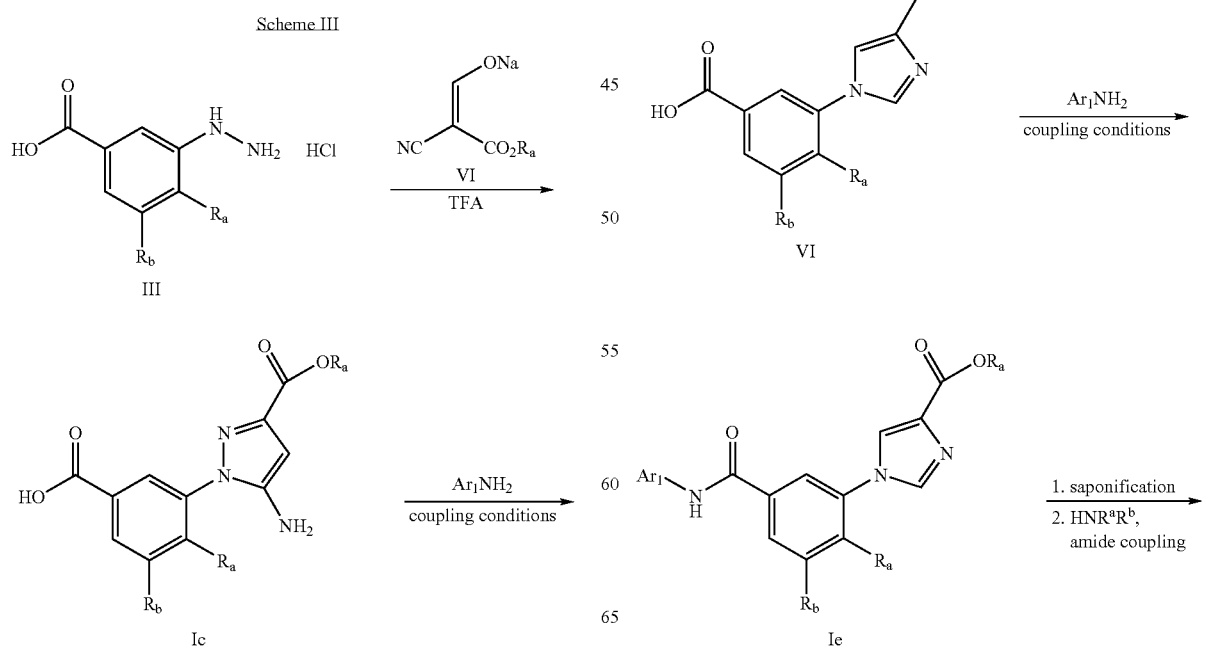

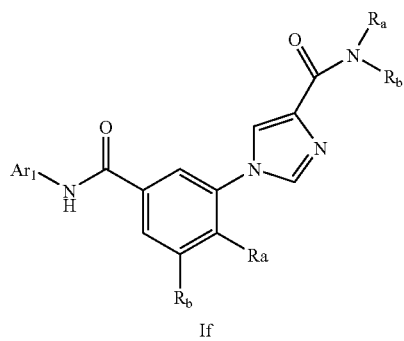

If

SYNTHETIC EXAMPLES

HPLC analyses were obtained using a Varian Dynamax C18 column or Phenomenex Luna C18 column with UV detection at 223 nm using a standard solvent gradient program.

| HPLC Method: | | | |
|---|---|---|---|
| Time (min) | Flow (mL/min) | % A | % B |
| 0.0 | 1.0 | 90.0 | 10.0 |
| 20.0 | 1.0 | 10.0 | 90.0 |
| 40.0 | 1.0 | 10.0 | 90.0 |
| 41.0 | 1.0 | 90.0 | 10.0 |

A = Water with 0.05% v/v Trifluoroacetic Acid
B = Acetonitrile with 0.05% v/v Trifluoroacetic Acid

Example 1

Synthesis of 5-amino-1-[5-(5-tert-butyl-3-methanesulfonylamino-2-methoxy-phenylcarbamoyl)-2-methyl-phenyl]-1H-pyrazole-3-carboxylic acid ethyl ester

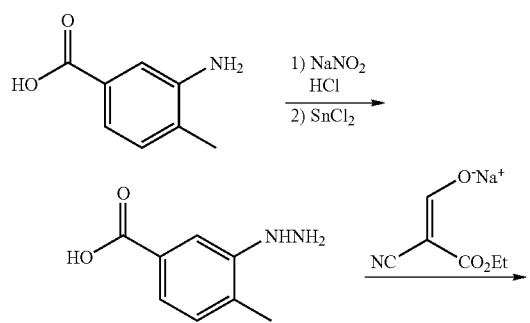

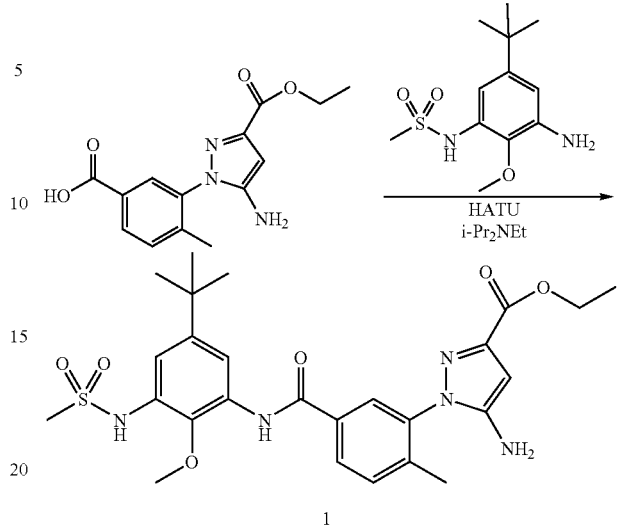

To a suspension of 3-amino-4-methylbenzoic acid (5.0 g, 33 mmol) in concentrated HCl (31 mL) cooled to below −5° C. was added a solution of NaNO$_2$ (2.4 g, 35 mmol) in water (12 mL) at such rate that the temperature remained below −4° C. After stirring for 45 min, the suspension was transferred to a cold stirred solution of SnCl$_2$ (28 g, 124 mmol) in concentrated HCl (18 mL) via pipette. The resulting solid was collected via vacuum filtration and washed first with cold water and then with Et$_2$O. The solid was recrystallized from water/2-propanol (10:1) to provide 3-hydrazino-4-methyl-benzoic acid hydrochloride. (2.23 g, 33%) as a pink solid. ESI MS m/z 167 [C$_8$H$_{10}$N$_2$O$_2$+H]$^+$.

To a solution of the above phenyl hydrazine intermediate, (50 mg, 0.247 mmol) in trifluoroacetic acid (TFA) (500 µL) was added sodium 2-cyano-1-ethoxycarbonyl-ethenol (49 mg, 0.298 mmol). The red mixture was heated to reflux for 2 h then cooled and concentrated. Purification by silica-gel chromatography (2% NH$_4$OH/25% MeOH in EtOAc) provided 5-amino-1-(5-carboxy-2-methyl-phenyl)-1H-pyrazole-3-carboxylic acid ethyl ester (60 mg, 83%) as a white solid: ESI MS m/z 290 [C$_{14}$H$_{15}$N$_3$O$_4$+H]$^+$.

5-Amino-1-(5-carboxy-2-methyl-phenyl)-1H-pyrazole-3-carboxylic acid ethyl ester (46 mg, 0.159 mmol) and O-(7-azabenzotriazol-1-yl)-N,N,N'N'-tetramethyluronium hexafluorophosphate (HATU) (67 mg, 0.175 mmol) were combined in DMF (500 µL) and stirred for 5 min at room temperature N-(3-amino-5-tert-butyl-2-methoxy-phenyl)-methanesulfonamide (48 mg, 0.175 mmol) was added to the reaction mixture followed by i-Pr$_2$NEt (83 µL, 0.477 mmol). The solution was stirred at room temperature for 48 h then poured onto saturated NaHCO$_3$. The aqueous layer was extracted with CH$_2$Cl$_2$ and the combined extracts were dried over Na$_2$SO$_4$, filtered, and concentrated. Purification by semi-prep HPLC provided the title compound (41 mg, 48%) as a yellow solid (TFA salt): mp 104-111° C. (dec.); ESI MS m/z 544 [C$_{26}$H$_{33}$N$_5$O$_6$S+H]$^+$; HPLC>98%, t$_R$=20.79 min.

Example 2

Synthesis of 1-[5-(5-tert-butyl-3-methanesulfonylamino-2-methoxy-phenylcarbamoyl)-2-methyl-phenyl]-1H-pyrazole-4-carboxylic acid ethyl ester

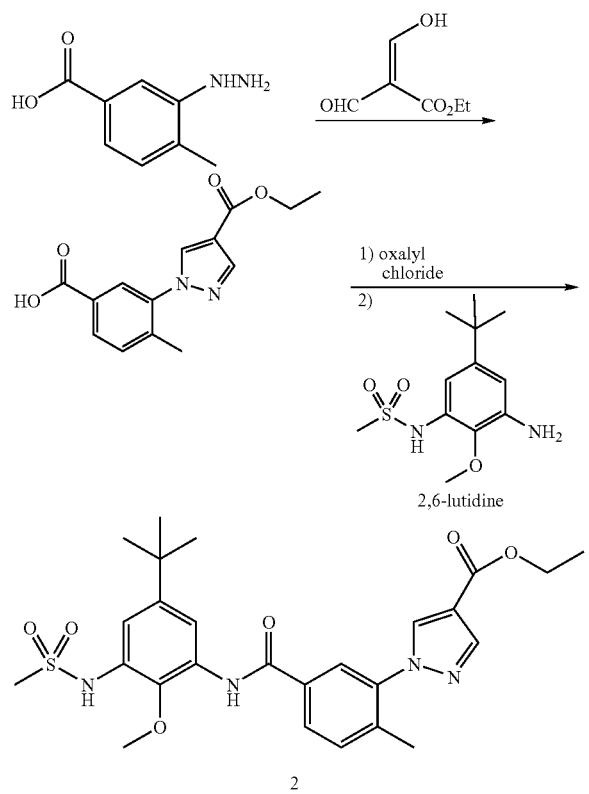

2

A solution of 2-formyl-3-oxo-propionic acid ethyl ester (Bertz, S. H.; Dabbagh, G.; Cotte, P. *J. Org. Chem.* 1982, 47, 2216) (1.44 g, 10 mmol) in EtOH (10 mL) was cooled in an ice bath. A slurry of 3-hydrazino-4-methyl-benzoic acid hydrochloride (2.02 g, 10 mmol) in EtOH (50 mL) was added and the reaction stirred overnight. The EtOH was removed under reduced pressure and the residue partitioned between water and $CH_2Cl_2$. The layers were separated and the organic layer washed with brine. The organic layer was dried over $Na_2SO_4$, filtered, and concentrated. Hexanes were added and the solution concentrated. The resulting solid was collected by vacuum filtration, washed with hexanes and dried under vacuum to provide 1-(5-carboxy-2-methyl-phenyl)-1H-pyrazole-4-carboxylic acid ethyl ester (1.86 g, 68%) as a yellow solid: ESI MS m/z 275 $[C_{14}H_{14}N_2O_4+H]^+$.

The above acid (617 mg, 2.25 mmol) was dissolved in 20 mL of $CH_2Cl_2$ and 7 mL of THF. One drop of dry DMF was added to the reaction. Oxalyl chloride (0.24 mL, 2.8 mmol) was carefully added via syringe and the reaction stirred 2 h. The solvents were removed under reduced pressure and then fresh $CH_2Cl_2$ (15 mL) was added. Then N-(3-amino-5-tert-butyl-2-methoxy-phenyl)-methanesulfonamide (666 mg, 2.15 mmol) was suspended in the solution and 2,6-lutidine (0.75 mL, 6.5 mmol) was added. The reaction was stirred for 2 h then was diluted with $CH_2Cl_2$. The mixture was washed with 1 M $NaHSO_4$ (2×), water, and finally $NaHCO_3$ solution. The solution was dried over $Na_2SO_4$, filtered, and concentrated. The resulting oil was triturated with diethyl ether and the solids collected by vacuum filtration, washed with diethyl ether, and dried under vacuum to provide the title compound (972 mg, 85%) as a white solid: mp 125-130° C.; ESI MS m/z 529 $[C_{26}H_{32}N_4O_6S+H]^+$, HPLC>95%, $t_R$=21.66 min.

Example 3

Synthesis of 1-[5-(5-tert-butyl-3-methanesulfonylamino-2-methoxy-phenylcarbamoyl)-2-methyl-phenyl]-1H-imidazole-4-carboxylic acid ethyl ester

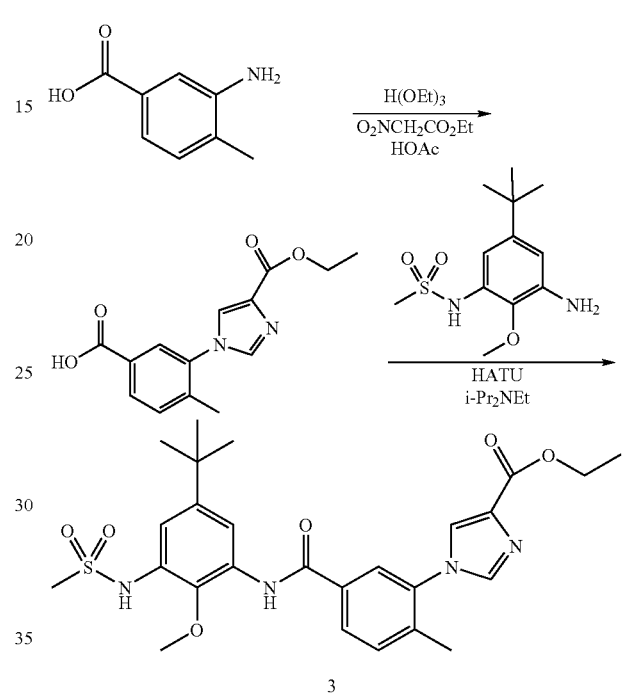

3

A slurry of 3-amino-4-methylbenzoic acid (5.00 g, 33.1 mmol), ethyl orthoformate (5.94 mL), ethyl nitroacetate (3.67 mL), and acetic acid (0.2 mL) was heated to 100° C. with stirring for 3.5 h. The mixture was cooled to 85° C. and an additional 66 mL each of ethyl orthoformate and acetic acid were added followed by 5.54 g (99.2 mmol) of iron powder. The mixture was heated to reflux and stirred for 1 h, when an additional 5.54 g of iron powder was added in three portions, each portion after 1 h of stirring at reflux. The mixture was then heated for an additional 6 h before being cooled to room temperature. The mixture was filtered and the solids were washed with EtOAc. The filtrate was collected and concentrated to afford a brown semisolid. The solid was triturated with $Et_2O$/EtOAc to provide 1.93 g (7.04 mmol, 21.3%) of 1-(5-carboxy-2-methyl-phenyl)-1H-imidazole-4-carboxylic acid ethyl ester as a tan solid.

To a cold solution of the above acid (1.00 g, 3.65 mmol), N-(3-amino-5-tert-butyl-2-methoxy-phenyl)-methanesulfonamide (993 mg, 3.65 mmol) and i-$Pr_2$NEt (2.13 mL) in 20 mL of DMF was added 3.71 g (7.30 mmol) of HATU. The mixture was allowed to warm to room temperature and was stirred overnight. The mixture was then partitioned between EtOAc and water, and the organic extract was washed with water and brine, then was dried with $MgSO_4$, filtered, and concentrated. Chromatography (0-5% (95:5 MeOH/$NH_4$OH) in dichloromethane) provided 849 mg (1.61 mmol, 44%) of the title compound; trituration of an aliquot with EtOAc/TBME provided analytically pure material.

Example 4

1-[5-(5-tert-Butyl-3-methanesulfonylamino-2-methoxy-phenylcarbamoyl)-2-methyl-phenyl]-1H-pyrazole-4-carboxylic acid (pyridin-3-ylmethyl)-amide

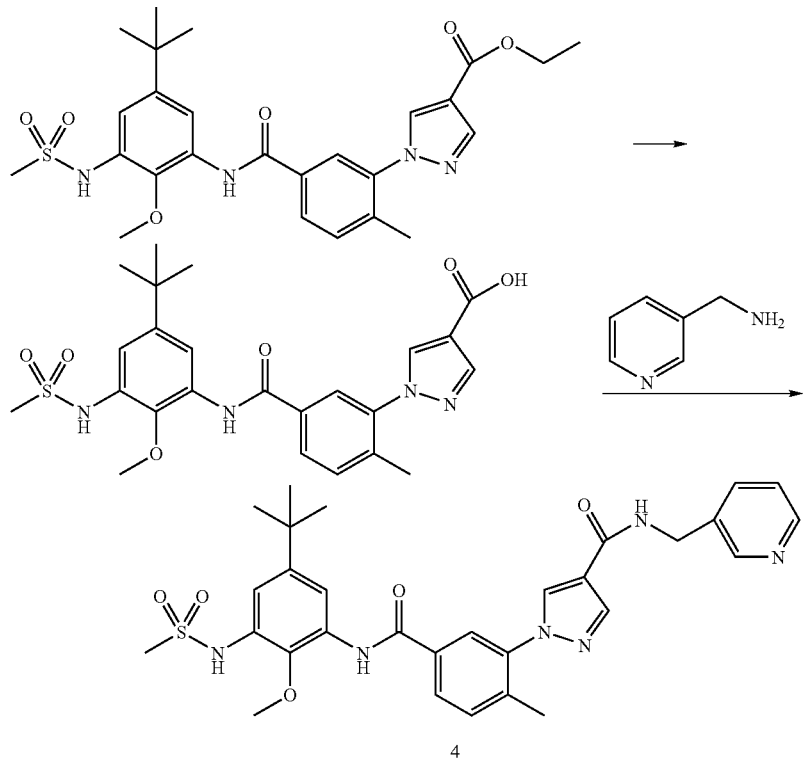

1-[5-(5-tert-butyl-3-methanesulfonylamino-2-methoxy-phenylcarbamoyl)-2-methyl-phenyl]-1H-pyrazole-4-carboxylic acid ethyl ester (Example 2) (900 mg) was suspended in MeOH (7 mL). A solution of 10% sodium hydroxide (33 mL) was added and the reaction stirred 2 h. The solution was acidified with concentrated HCl to a pH of 4 resulting in a suspension. The suspension was cooled in an ice bath and the solids collected by vacuum filtration. The solids were washed with water, dried under vacuum over $P_2O_5$ at 50° C. to provide 1-[5-(5-tert-butyl-3-methanesulfonylamino-2-methoxy-phenylcarbamoyl)-2-methyl-phenyl]-1H-pyrazole-4-carboxylic acid (782 mg, 91%) as a white solid.

The above carboxylic acid (75 mg, 0.15 mmol), 3-(aminomethyl)pyridine (25 mg, 0.23 mmol) and HATU (85 mg, 0.23 mmol) were dissolved in DMF (1.5 mL). N,N-Diisopropylethylamine (78 μL, 0.45 mmol) was added and the reaction was stirred overnight. Water was added and the resulting solution was extracted with $CH_2Cl_2$ (4×30 mL). The combined organic extracts were washed with 5% LiCl solution, dried over $MgSO_4$, filtered, and concentrated. The residue was purified by semi-prep HPLC. The product fractions were concentrated and sodium bicarbonate added. The resulting solid was collected by vacuum filtration, washed with water, and dried under vacuum at 55° C. to provide the title compound (48 mg, 54%) as white solid: mp 127-133° C.; ESI MS m/z 591 $[C_{30}H_{34}N_6O_5S+H]^+$; HPLC>95%, $t_R$=15.03 min.

The following were prepared in the same manner as described in the above example, by coupling the intermediate carboxylic acid with the appropriate amine:

| | Amine | Product |
|---|---|---|
| Example 4a | $H_2N$—CH₂-(4-pyridyl) | 1-[5-(5-tert-Butyl-3-methanesulfonylamino-2-methoxy-phenylcarbamoyl)-2-methyl-phenyl]-1H-pyrazole-4-carboxylic acid (pyridin-4-ylmethyl)-amide: mp 126-130° C.; ESI MS m/z 591 $[C_{30}H_{34}N_6O_5S + H]^+$; HPLC >95%, $t_R$ = 14.98 min. |

| | Amine | Product |
|---|---|---|
| Example 4b | cyclopentylmethylamine | 1-[5-(5-tert-Butyl-3-methanesulfonylamino-2-methoxy-phenylcarbamoyl)-2-methyl-phenyl]-1H-pyrazole-4-carboxylic acid cyclopentylmethyl-amide: mp 195-198° C.; ESI MS m/z 582 [$C_{30}H_{39}N_5O_5S$ + H]$^+$; HPLC >95%, $t_R$ = 22.82 min. |
| Example 4c | 3-dimethylamino-2,2-dimethylpropylamine | 1-[5-(5-tert-Butyl-3-methanesulfonylamino-2-methoxy-phenylcarbamoyl)-2-methyl-phenyl]-1H-pyrazole-4-carboxylic acid (3-dimethylamino-2,2-dimethyl-propyl)-amide: mp 108-110° C.; ESI MS m/z 613 [$C_{31}H_{44}N_6O_5S$ + H]$^+$; HPLC >95%, $t_R$ = 15.43 min. |
| Example 4d | neopentylamine | 1-[5-(5-tert-Butyl-3-methanesulfonylamino-2-methoxy-phenylcarbamoyl)-2-methyl-phenyl]-1H-pyrazole-4-carboxylic acid (2,2-dimethyl-propyl)-amide; 207-208° C.; ESI MS m/z 570 [$C_{29}H_{39}N_5O_5S$ + H]$^+$, HPLC >95%, $t_R$ = 20.73 min. |
| Example 4e | (R)-1-phenylethylamine | 1-[5-(5-tert-Butyl-3-methanesulfonylamino-2-methoxy-phenylcarbamoyl)-2-methyl-phenyl]-1H-pyrazole-4-carboxylic acid ((R)-1-phenyl-ethyl)-amide; mp 135-138° C.; ESI MS m/z 604 [$C_{32}H_{37}N_5O_5S$ + H]$^+$; HPLC >95%, $t_R$ = 20.84 min. |

Example 5

Synthesis of 1-[5-(5-tert-butyl-3-methanesulfonylamino-2-methoxy-phenylcarbamoyl)-2-methyl-phenyl]-1H-imidazole-4-carboxylic acid (2,2-dimethyl-propyl)-amide

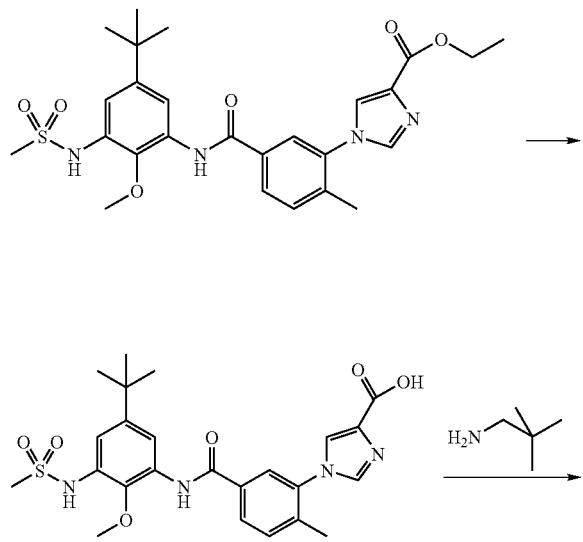

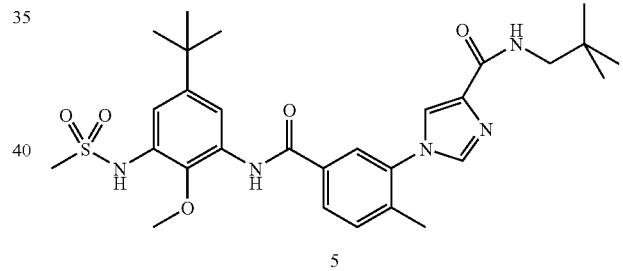

1-[5-(5-tert-butyl-3-methanesulfonylamino-2-methoxy-phenylcarbamoyl)-2-methyl-phenyl]-1H-imidazole-4-carboxylic acid ethyl ester (Example 3) (820 mg, 1.55 mmol) was dissolved in 5 mL of cold MeOH and a solution of 130 mg (3.10 mmol) of LiOH-H$_2$O in 3 mL of water was added dropwise. The mixture was allowed to warm to room temperature and was then stirred for 4 h. A 1 N HOAc solution (3.2 mL) was then added and the mixture was diluted with 30 mL of water, and then was extracted with 75 mL of EtOAc. The extract was washed with water and brine, was dried with MgSO$_4$, filtered, and concentrated to provide 631 mg (1.26 mmol, 81%) of 1-[5-(5-tert-butyl-3-methanesulfonylamino-2-methoxy-phenylcarbamoyl)-2-methyl-phenyl]-1H-imidazole-4-carboxylic acid.

The above carboxylic acid was then coupled with neopentylamine using the coupling procedure described in Example 4 to provide the title compound. 134-136° C.; ESI MS m/z 570 [$C_{29}H_{39}N_5O_5S$ +H]$^+$.

The following compounds may also be prepared by using the methods described for Examples 1-5 by using 1-(5-carboxy-2-methyl-phenyl)-1H-imidazole-4-carboxylic acid ethyl ester and the appropriate aniline and amine.

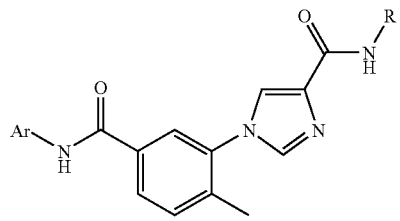

| Name | Aniline (ArNH₂) | Amine (RNH₂) |
|---|---|---|
| 1-[5-(2-Methoxy-5-trifluoromethyl-phenylcarbamoyl)-2-methyl-phenyl]-1H-imidazole-4-carboxylic acid (2,2-dimethyl-propyl)-amide | | |
| 1-[5-(3-Acetylamino-5-tert-butyl-2-methoxy-phenylcarbamoyl)-2-methyl-phenyl]-1H-imidazole-4-carboxylic acid (2,2-dimethyl-propyl)-amide | | |
| 1-[5-(3-Amino-5-tert-butyl-2-methoxy-phenylcarbamoyl)-2-methyl-phenyl]-1H-imidazole-4-carboxylic acid (2,2-dimethyl-propyl)-amide | | |
| 1-[5-(3-Methanesulfonylamino-2-methoxy-5-trifluoromethyl-phenylcarbamoyl)-2-methyl-phenyl]-1H-imidazole-4-carboxylic acid (2,2-dimethyl-propyl)-amide | Note 1 | |
| 1-[5-(5-tert-Butyl-2-methyl-pyridin-3-ylcarbamoyl)-2-methyl-phenyl]-1H-imidazole-4-carboxylic acid (2,2-dimethyl-propyl)-amide | Note 2 | |

-continued

| Name | Aniline (ArNH₂) | Amine (RNH₂) |
|---|---|---|
| 1-[5-(5-ter-Butyl-3-cyano-2-methoxy-phenylcarbamoyl)-2-methyl-phenyl]-1H-imidazole-4-carboxylic acid (2,2-dimethyl-propyl)-amide | [structure: 5-tert-butyl-3-cyano-2-methoxy aniline] Note 2 | [structure: neopentylamine] |
| 1-[5-(5-tert-Butyl-3-methanesulfonylamino-2-methoxy-phenylcarbamoyl)-2-methyl-phenyl]-1H-imidazole-4-carboxylic acid ((S)-1-phenyl-ethyl)-amide | [structure: 5-tert-butyl-3-methanesulfonylamino-2-methoxy aniline] | [structure: (S)-1-phenylethylamine] |
| 1-[5-(5-tert-Butyl-3-methanesulfonylamino-2-methoxy-phenylcarbamoyl)-2-methyl-phenyl]-1H-imidazole-4-carboxylic acid ((R)-1-phenyl-ethyl)-amide | [structure: 5-tert-butyl-3-methanesulfonylamino-2-methoxy aniline] | [structure: (R)-1-phenylethylamine] |
| 1-[5-(5-tert-Butyl-3-methanesulfonylamino-2-methoxy-phenylcarbamoyl)-2-methyl-phenyl]-1H-imidazole-4-carboxylic acid (pyridin-3-ylmethyl)-amide | [structure: 5-tert-butyl-3-methanesulfonylamino-2-methoxy aniline] | [structure: 3-(aminomethyl)pyridine] |
| 1-[5-(5-tert-Butyl-3-methanesulfonylamino-2-methoxy-phenylcarbamoyl)-2-methyl-phenyl]-1H-imidazole-4-carboxylic acid (3-dimethylamino-2,2-dimethyl-propyl)-amide | [structure: 5-tert-butyl-3-methanesulfonylamino-2-methoxy aniline] | [structure: 3-dimethylamino-2,2-dimethyl-propylamine] |

-continued

| Name | Aniline (ArNH$_2$) | Amine (RNH$_2$) |
|---|---|---|
| 1-[5-(5-tert-Butyl-3-methanesulfonylamino-2-methyl-phenylcarbamoyl)-2-methyl-phenyl]-1H-imidazole-4-carboxylic acid (2,2-dimethyl-propyl)-amide | Note 3 | |
| 1-{5-[3-Methanesulfonylamino-2-methoxy-5-(1-methyl-cyclopropyl)-phenylcarbamoyl]-2-methyl-phenyl}-1H-imidazole-4-carboxylic acid (2,2-dimethyl-propyl)-amide | Note 3 | |
| 1-{5-[5-tert-Butyl-2-((R)-methanesulfinyl)-phenylcarbamoyl]-2-methyl-phenyl}-1H-imidazole-4-carboxylic acid (2,2-dimethyl-propyl)-amide | Note 2 | |
| 1-{5-[5-tert-Butyl-2-((S)-methanesulfinyl)-phenylcarbamoyl]-2-methyl-phenyl}-1H-imidazole-4-carboxylic acid (2,2-dimethyl-propyl)-amide | Note 2 | |

Note 1: US 2004-0077647

Note 2: US provisional application 60/567,693

Note 3: US provisional application 60/453,364.

The following compounds may also be prepared by using the methods described for Examples 1-5 by using 1-(5-carboxy-2-methyl-phenyl)-1H-pyrazole-4-carboxylic acid ethyl ester and the appropriate aniline and amine.

| Name | Aniline (ArNH$_2$) | Amine (RNH$_2$) |
| --- | --- | --- |
| 1-[5-(2-Methoxy-5-trifluoromethyl-phenylcarbamoyl)-2-methyl-phenyl]-1H-pyrazole-4-carboxylic acid (2,2-dimethyl-propyl)-amide | | |
| 1-[5-(3-Acetylamino-5-tert-butyl-2-methoxy-phenylcarbamoyl)-2-methyl-phenyl]-1H-pyrazole-4-carboxylic acid (2,2-dimethyl-propyl)-amide | | |
| 1-[5-(3-Amino-5-tert-butyl-2-methoxy-phenylcarbamoyl)-2-methyl-phenyl]-1H-pyrazole-4-carboxylic acid (2,2-dimethyl-propyl)-amide | | |
| 1-[5-(3-Methanesulfonylamino-2-methoxy-5-trifluoromethyl-phenylcarbamoyl)-2-methyl-phenyl]-1H-pyrazole-4-carboxylic acid (2,2-dimethyl-propyl)-amide | | |

Note 1

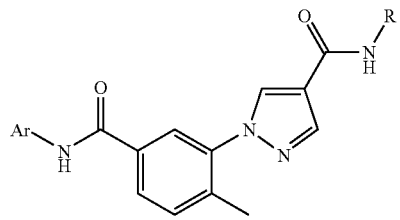

| Name | Aniline (ArNH$_2$) | Amine (RNH$_2$) |
| --- | --- | --- |
| 1-[5-(5-tert-Butyl-2-methyl-pyridin-3-ylcarbamoyl)-2-methyl-phenyl]-1H-pyrazole-4-carboxylic acid (2,2-dimethyl-propyl)-amide | (structure) Note 2 | (structure) |
| 1-[5-(5-tert-Butyl-3-cyano-2-methoxy-phenylcarbamoyl)-2-methyl-phenyl]-1H-pyrazole-4-carboxylic acid (2,2-dimethyl-propyl)-amide | (structure) Note 2 | (structure) |
| 1-[5-(5-tert-Butyl-3-methanesulfonylamino-2-methoxy-phenylcarbamoyl)-2-methyl-phenyl]-1H-pyrazole-4-carboxylic acid ((S)-1-phenyl-ethyl)-amide | (structure) | (structure) |
| 1-{5-[3-Methanesulfonylamino-2-methoxy-5-(1-methyl-cyclopropyl)-phenylcarbamoyl]-2-methyl-phenyl}-1H-pyrazole-4-carboxylic acid (2,2-dimethyl-propyl)-amide | (structure) Note 3 | (structure) |

-continued

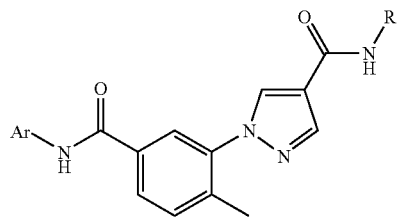

| Name | Aniline (ArNH$_2$) | Amine (RNH$_2$) |
|---|---|---|
| 1-{5-[5-tert-Butyl-2-((R)-methanesulfinyl)-phenylcarbamoyl]-2-methyl-phenyl}-1H-pyrazole-4-carboxylic acid (2,2-dimethyl-propyl)-amide | Note 2 | |
| 1-{5-[5-tert-Butyl-2-((S)-methanesulfinyl)-phenylcarbamoyl]-2-methyl-phenyl}-1H-pyrazole-4-carboxylic acid (2,2-dimethyl-propyl)-amide | Note 2 | |

Note 1: US 2004-0077647
Note 2: US provisional application 60/567,693
Note 3: US provisional application 60/453,364

Methods of Use

In accordance with the invention, there are provided novel methods of using the compounds of the formula (I). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. The compounds of the invention may also be useful for anticoagulant or fibrinolytic therapy (and the diseases or conditions related to such therapy) as described in the provisional application No. 60/403,422.

The compounds of the invention are also p38 MAP kinase inhibitors. Activity can be demonstrated by using methods known in the art. See for example Branger et al., (2002) *J Immunol.* 168: 4070-4077, and the 46 references cited therein, each incorporated herein by reference in their entirety. As disclosed in the Background of the Invention, the compounds of the invention will therefore be useful for treating inflammatory and oncological diseases. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non- Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822, PCT/US 01/21860 and U.S. application Ser. No. 10/214,782, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed, Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. Reference in this regard may also be made to U.S. provisional application Ser. No. 60/339,249. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Biological Assays

Inhibition of TNF Production in THP Cells

The inhibition of cytokine production can be observed by measuring inhibition of TNFα in lipopolysaccharide stimulated THP cells (for example, see W. Prichett et al, 1995, *J. Inflammation,* 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was non-sterile. Initial stock solutions were made in DMSO followed by dilution into RPMI 1640 2-fold higher than the desired final assay concentration. Confluent THP.1 cells ($2\times10^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 μg/ml final; Siga L-2630, from *E. coli* serotype 0111.B4; stored as 1 mg/ml stock in endotoxin screened distilled $H_2O$ at −80° C.). Blanks (unstimulated) received $H_2O$ vehicle; final incubation volume was 250 μl. Overnight incubation (18-24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc, Cary, N.C.). The calculated $IC_{50}$ value is the concentration of the test compound that caused a 50% decrease in the maximal TNFα production.

Preferred compounds have an $IC_{50}$<1 uM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1beta, GM-CSF, IL-6 and IL-8 can be demonstrated for preferred compounds (for example, see J. C. Lee et al, 1988, *Int. J. Immunopharmacol*, 10, 835).

All references disclosed in this application including patents, patent publications and literature citations are incorporated herein by reference in their entirety.

What is claimed is:

1. A compound of the formula (I)

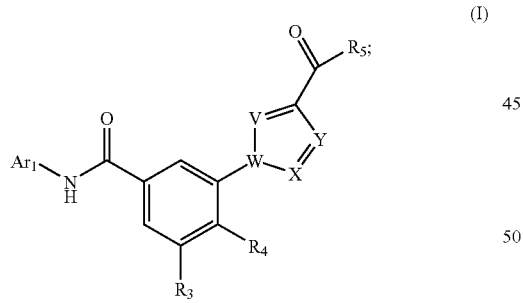

wherein:
the cyclic moiety is

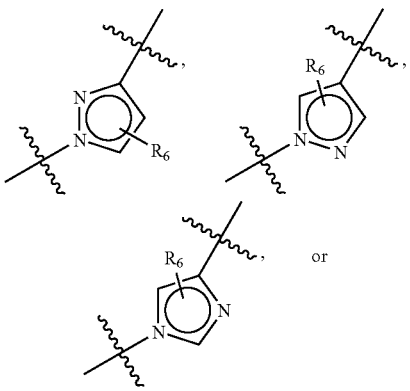

where $R_6$ can be covalently attached to any position on the ring where possible;

$Ar_1$ is chosen from (i), (ii) and (iii) below:

i) a carbocycle substituted by $R_1$, $R_2$ and $R_x$,

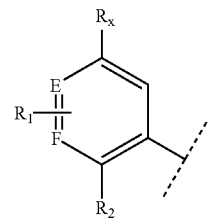

wherein one of E or F is nitrogen and the other is carbon, $R_1$ is covalently attached to either E or F, and when nitrogen is N—$R_1$ the double bond between E and F is not present;

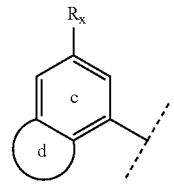

wherein c is a benzo ring fused to ring d which is a 5-7 membered heterocyclic ring optionally substituted by an oxo (═O) group and one to two R groups each independently being hydrogen or C1-3 alkyl;

$R_1$ is chosen from hydrogen, $NO_2$, —N$(R_c)_2$, —$(CH_2)_n$—C(O)—N$(R_a)_2$, —$(CH_2)_n$—N$(R_a)_2$, J-C(O)—N$(R_c)$—, J-S(O)$_m$—N$(R_c)$—, C1-6 alkylS(O)$_m$— or $R_1$ is chosen from C1-6 alkyl, C3-7 cylcoalkyl, C1-5 alkoxy or C3-7 cycloalkoxy, C1-5 alkylthiol or C3-7 cycloalkylthiol, C1-5 acyl, C1-5 alkoxycarbonyl, C1-5 acyloxy, C1-5 acylamino, C2-5 alkenyl, C2-5 alkynyl, heterocycle, heterocycleC1-6 alkyl, heteroaryl, heteroarylC 1-6 alkyl and nitrile; each of the aforementioned where possible are optionally partially or fully halogenated or are optionally further substituted with alkylsulfonylamino, aminocarboxyl, alkoxyl, amino, alkylamino, dialkylamino, hydroxyl, oxo, nitro or nitrile;

J is chosen from C1-10 alkyl and carbocycle each optionally substituted by $R_b$;

$R_2$ is chosen from:
hydrogen, halogen, nitrile, C1-5 alkylS(O)$_m$—, arylS(O)$_m$, J-O—C(O)—O—, N($R_c$)$_2$—C(O)—(CH$_2$)$_n$—, C1-6 acetyl, aroyl, C1-6alkoxycarbonyl, C1-6 alkyl, C3-7cycloalkyl, C1-6 alkoxy, C3-5cycloalkoxy, C1-5 alkylC1-5 alkoxy, hydroxy, hydroxy C1-5 alkyl, and amino optionally mono- or di-substituted by C1-5 alkyl, aryl or aryl C1-5 alkyl; each of the aforementioned where possible are optionally partially or fully halogenated or are optionally further substituted with C1-3 alkyl, alkylsulfonylamino, alkoxyl, amino, alkylamino, dialkylamino, hydroxyl, oxo, nitro or nitrile;

each $R_x$ is chosen from C1-6 alkyl or C3-7 cycloalkyl each being optionally substituted by C1-3 alkyl and optionally partially or fully halogenated, C1-4 acyl, aroyl, C1-4 alkoxy, C1-5alkylS(O)$_m$—, each may optionally be partially or fully halogenated, halogen, C1-6 alkoxycarbonyl, carbocyclesulfonyl;

each $R_c$ is independently hydrogen or C1-5 alkyl;

$R_3$, $R_4$, $R_6$, $R_7$ and $R_8$ are each independently chosen from hydrogen, halogen, C1-5 alkyl, C1-5 alkoxy, C1-5 alkylC1-5 alkoxy, hydroxy, hydroxy C1-5 alkyl or amino optionally mono- or di-substituted by C1-5 alkyl, aryl or aryl C1-5 alkyl;

$R_5$ is:
$R_a$, —O—$R_a$, —S—$R_a$, —N($R_a$)$_2$, —C(O)—$R_a$, —NH(CR$_7$R$_8$)$_n$—$R_a$, —(CR$_7$R$_8$)$_n$—N($R_a$)$_2$, —(CR$_7$R$_8$)$_n$—$R_a$, —O(CR$_7$R$_8$)$_n$—$R_a$, —C(O)—O(CR$_7$R$_8$)$_n$—$R_a$, —C(O)(CR$_7$R$_8$)$_n$—$R_a$ and —C(O)NH(CR$_7$R$_8$)$_n$—;

or $R_5$ is a ring system chosen from aryl, heteroaryl or heterocyclyl each optionally substituted by $R_a$;

$R_a$ and $R_b$ are each independently chosen from hydrogen, C1-5 alkyl, hydroxyC1-5 alkyl, C2-5 alkenyl, C2-5 alkynyl, carbocycle, heterocycle, heteroaryl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, each of the aforementioned are optionally partially or fully halogenated, or $R_a$ and $R_b$ are chosen from C1-5 alkylsulphonylamino, hydroxy, oxo, halogen, nitro and nitrile, wherein each carbocycle, heterocycle or heteroaryl for $R_a$ and $R_b$ is optionally substituted by amino, C1-3 alkyl, halogen or hydroxy;

n is 1-5;

m is 0, 1 or 2;

and

X is O or S or the pharmaceutically acceptable salts thereof.

2. The compound according to claim 1 wherein:

J is chosen from C1-10 alkyl, aryl and C3-7 cycloalkyl each optionally substituted by $R_b$;

$R_2$ is independently chosen from hydrogen, J-O—C(O)—O—, C1-6 alkoxy, C1-6 alkyl, C1-6 acetyl, aroyl, halogen, methoxycarbonyl, phenylsulfonyl, C1-5 alkylS(O)$_m$— and C3-7 cycloalkyl optionally substituted by C1-3 alkyl, each $R_2$ where possible may be optionally partially or fully halogenated;

$R_1$ is chosen from hydrogen, C1-6 alkyl, C1-5 alkylS(O)$_m$—, J-S(O)$_m$—N($R_c$)—, C1-5 alkoxy, C1-5 alkylthiol, NH$_2$—C(O)—(CH$_2$)$_n$—, ($R_c$)$_2$N C1-6 alkyl, C1-5acylNH—, —NH$_2$, —NO$_2$, heteroaryl chosen from pyrazole, triazole, imidazole and tetrazole, and nitrile;

ring d is a 5-6 membered heterocyclic ring such that rings c and d fuse to form the following:

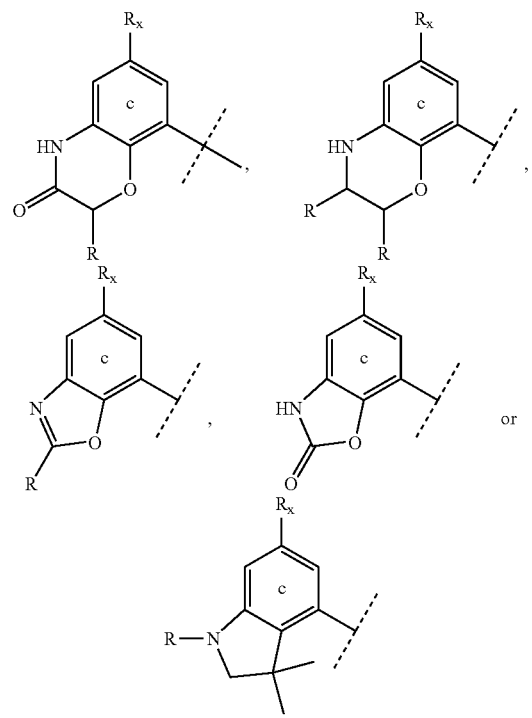

where each R is independently hydrogen or C1-3 alkyl;

$R_3$ and $R_4$ are each independently chosen from hydrogen, C1-3 alkoxy, C1-3 alkyl and halogen;

n is 1-4;

$R_a$ and $R_b$ are each independently chosen from hydrogen, C1-5 alkyl, C2-5 alkenyl, C2-5 alkynyl, C3-8 cycloalkylC0-2 alkyl, aryl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, C1-5 sulphonylamino, hydroxy, halogen, CF$_3$, CH$_2$-CF$_3$, nitro, nitrile or $R_a$ and $R_b$ are chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone and heteroaryl chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]

pyridinyl; wherein each aryl, heterocycle or heteroaryl for $R_a$ and $R_b$ is optionally substituted by amino, C1-3 alkyl, halogen or hydroxyl;

and X is O.

3. The compound according to claim 2 wherein:

$R_5$ is:

$R_a$, —O—$R_a$, —S—$R_a$, —N($R_a$)$_2$, —C(O)—$R_a$, —NH(CR$_7$R$_8$)$_n$—$R_a$, —(CR$_7$R$_8$)$_n$—N($R_a$)$_2$, —(CR$_7$R$_8$)$_n$—$R_a$, —O(CR$_7$R$_8$)$_n$—$R_a$, —C(O)—O(CR$_7$R$_8$)$_n$—$R_a$, —C(O)(CR$_7$R$_8$)$_n$—$R_a$ and —C(O)NH(CR$_7$R$_8$)$_n$—, wherein n is 1-3;

$R_7$ and $R_8$ are each independently chosen from hydrogen, halogen, C1-5 alkyl, C1-5 alkoxy, C1-5 alkylC1-5 alkoxy, hydroxy, hydroxy C1-5 alkyl or amino optionally mono- or di-substituted by C1-5 alkyl, phenyl or phenylC1-5 alkyl.

4. The compound according to claim 3 wherein:

$Ar_1$ is:

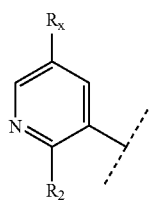

or $Ar_1$ is cyclobutyl, phenyl, naphthyl, tetrahydronaphthyl, indanyl and indenyl each substituted with one $R_1$, one $R_x$, and one $R_2$ group;

$R_1$ is hydrogen, nitrile, NO$_2$, NH$_2$, C1-3acylNH—, J-S(O)$_m$—N($R_c$)— where J is C1-10 alkyl, or $R_1$ is

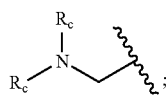

$R_2$ is independently chosen from C1-6 alkyl, C1-6 alkylS(O)$_m$—, C1-3 alkoxy and C3-6 cycloalkyl optionally substituted by C1-3 alkyl, each may optionally be partially or fully halogenated;

$R_3$ and $R_4$ are each independently chosen from hydrogen, C1-3 alkyl, fluoro and chloro;

$R_6$ is chosen from hydrogen and amino;

n is 1-2;

$R_a$ and $R_b$ are each independently chosen from hydrogen, C1-5 alkyl, C3-7 cycloalkylC0-2 alkyl, aryl, C1-5 alkoxy, amino, C1-5 alkylamino, C1-5 dialkylamino, C1-3 acyl, C1-5 alkoxycarbonyl, C1-3 acyloxy, C1-3 acylamino, C1-3 sulphonylamino, hydroxy, halogen, CF$_3$, CH$_2$—CF$_3$, nitro, nitrile;

or $R_a$ is chosen from pyrrolidinyl, pyrrolinyl, morpholinyl, thiomorpholinyl, thiomorpholinyl sulfoxide, thiomorpholinyl sulfone, piperidinyl, piperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl ; wherein each aryl, heterocycle or heteroaryl for $R_a$ and $R_b$ is optionally substituted by amino, C1-3 alkyl, halogen or hydroxyl.

5. The compound according to claim 4 wherein:

$Ar_1$ is

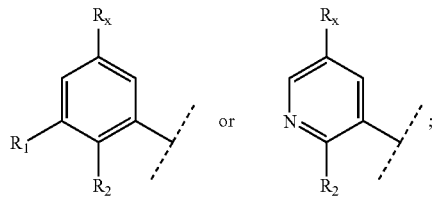

$R_1$ is:

hydrogen, J-S(O)$_2$—NH—, where J is C1-5 alkyl, or $R_1$ is nitrile, NO$_2$, NH$_2$ or C1-3acylNH—;

wherein $R_x$=$R_2$ each are independently chosen from C1-5 alkyl, C1-5 alkylS(O)$_m$—, C1-4 alkoxy and and C3-5 cycloalkyl optionally substituted by C1-2 alkyl, each may optionally be partially or fully halogenated.

6. The compound according to claim 5 wherein:

$R_a$ is chosen from hydrogen, C1-5 alkyl, C3-6 cycloalikylC0-2 alkyl, phenyl, C1-5 alkoxy, amino, C1-5 alkylamino, C1-5 dialkylamino, C1-3 acyl, C1-5 alkoxycarbonyl, C1-3 acyloxy, C1-3 acylamino, hydroxy, halogen;

or $R_a$ is chosen from morpholinyl, thiomorpholinyl, thiomorpholinyl sulfoxide, thiomorpholinyl sulfone, piperidinyl, piperidinonyl, pyridinyl, pyrimidinyl, pyrazinyl and pyridazinyl wherein each are optionally substituted by amino, C1-3 alkyl, halogen or hydroxyl.

7. The compound according to claim 6 wherein:

$R_a$ is chosen from hydrogen, C1-5 alkyl, C3-6 cycloalkyl, phenyl, C1-5 alkoxy, C1-5 alkoxycarbonyl, C1-3 acyloxy, C1-3 acylamino, amino, mono-or-di-C1-4 alkyl amino, hydroxy, halogen;

or $R_a$ is chosen morpholinyl, piperidinyl and pyridinyl wherein each are optionally substituted by amino, C1-3 alkyl, halogen or hydroxyl.

8. The compound according to claim 7 wherein:

$Ar_1$ is

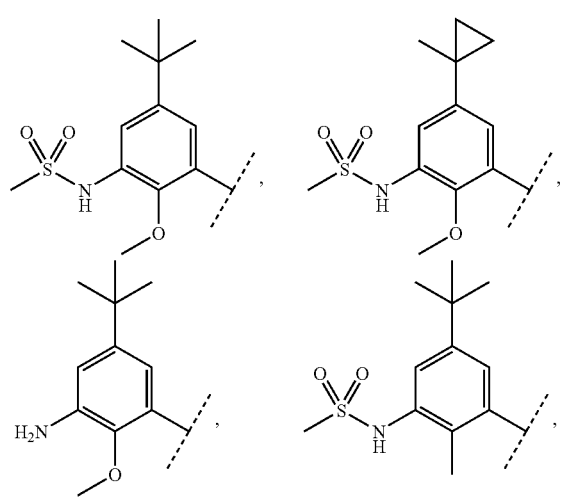

-continued

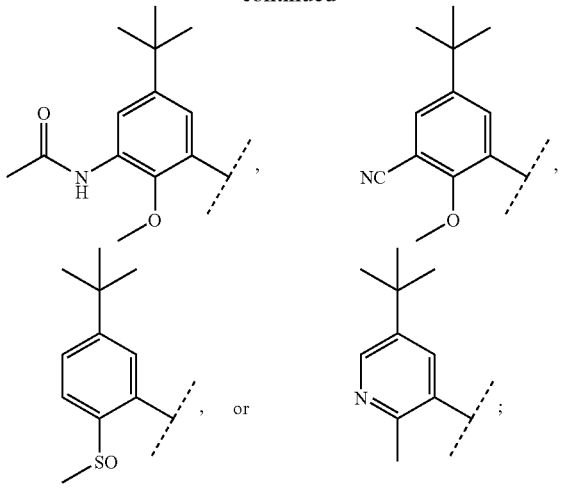

R₅ is:
C1-4 alkyl, C3-6 cycloalkyl, morpholinyl(CH₂)₁₋₂—, halogen, C1-3 alkoxy, hydroxy, —N(R$_a$)₂, —CF₃, —CH₂—CF₃, piperidinyl, phenyl, phenyl—S(O)$_m$— or benzyl each phenyl, heteroaryl or heterocyclic group is optionally substituted by C1-3 alkyl, halogen or hydroxy, or R₅ is —NH(CR₇R₈)$_n$—R$_a$ or —(CR₇R₈)$_n$—N(R$_a$)₂ wherein R$_a$ is chosen from hydrogen, phenyl, morpholinyl, piperidinyl, pyridinyl, amino, mono-or-di-C1-3 alkyl amino, cyclopropyl, cyclopentyl, cyclohexyl, C1-5 alkyl and C1-3 alkoxy.

9. A compound chosen from:
1-[5-(2-Methoxy-5-trifluoromethyl-phenylcarbamoyl)-2-methyl-phenyl]-1H-imidazole-4-carboxylic acid (2,2-dimethyl-propyl)-amide;
1-[5-(2-Methoxy-5-trifluoromethyl-phenylcarbamoyl)-2-methyl-phenyl]-1H-pyrazole-4-carboxylic acid (2,2-dimethyl-propyl)-amide;
1-[5-(3-Acetylamino-5-tert-butyl-2-methoxy-phenylcarbamoyl)-2-methyl-phenyl]-1H-imidazole-4-carboxylic acid (2,2-dimethyl-propyl)-amide;
1-[5-(3-Acetylamino-5-tert-butyl-2-methoxy-phenylcarbamoyl)-2-methyl-phenyl]-1H-pyrazole-4-carboxylic acid (2,2-dimethyl-propyl)-amide;
1-[5-(3-Amino-5-tert-butyl-2-methoxy-phenylcarbamoyl)-2-methyl-phenyl]-1H-imidazole-4-carboxylic acid (2,2-dimethyl-propyl)-amide;
1-[5-(3-Amino-5-tert-butyl-2-methoxy-phenylcarbamoyl)-2-methyl-phenyl]-1H-pyrazole-4-carboxylic acid (2,2-dimethyl-propyl)-amide;
1-[5-(3-Methanesulfonylamino-2-methoxy-5-trifluoromethyl-phenylcarbamoyl)-2methyl-phenyl]-1H-imidazole-4-carboxylic acid (2,2-dimethyl-propyl)-amide;
1-[5-(3-Methanesulfonylamino-2-methoxy-5-trifluoromethyl-phenylcarbamoyl)-2methyl-phenyl]-1H-pyrazole-4-carboxylic acid (2,2-dimethyl-propyl)-amide;
1-[5-(5-tert-Butyl-2-methyl-pyridin-3-ylcarbamoyl)-2-methyl-phenyl]-1H-imidazole-4-carboxylic acid (2,2-dimethyl-propyl)-amide;
1-[5-(5-tert-Butyl-2-methyl-pyridin-3-ylcarbamoyl)-2-methyl-phenyl]-1H-pyrazole-4-carboxylic acid (2,2-dimethyl-propyl)-amide;
1-[5-(5-tert-Butyl-3-cyano-2-methoxy-phenylcarbamoyl)-2-methyl-phenyl]-1H-imidazole-4-carboxylic acid (2,2-dimethyl-propyl)-amide;
1-[5-(5-tert-Butyl-3-cyano-2-methoxy-phenylcarbamoyl)-2-methyl-phenyl]-1H-pyrazole-4-carboxylic acid (2,2-dimethyl-propyl)-amide;
1-[5-(5-tert-Butyl-3-methanesulfonylamino-2-methoxy-phenylcarbamoyl)-2-methyl-phenyl]-1H-pyrazole-4-carboxylic acid ethyl ester;
1-[5-(5-tert-Butyl-3-methanesulfonylamino-2-methoxy-phenylcarbamoyl)-2-methyl-phenyl]-1H-pyrazole-4-carboxylic acid ((R)-1-phenyl-ethyl)-amide;
1-[5-(5-tert-Butyl-3-methanesulfonylamino-2-methoxy-phenylcarbamoyl)-2-methyl-phenyl]-1H-pyrazole-4-carboxylic acid ((S)-1-phenyl-ethyl)-amide;
1-[5-(5-tert-Butyl-3-methanesulfonylamino-2-methoxy-phenylcarbamoyl)-2-methyl-phenyl]-1H-pyrazole-4-carboxylic acid (2,2-dimethyl-propyl)-amide;
1-[5-(5-tert-Butyl-3-methanesulfonylamino-2-methoxy-phenylcarbamoyl)-2-methyl-phenyl]-1H-pyrazole-4-carboxylic acid (pyridin-4-ylmethyl)-amide;
1-[5-(5-tert-Butyl-3-methanesulfonylamino-2-methoxy-phenylcarbamoyl)-2-methyl-phenyl]-1H-pyrazole-4-carboxylic acid cyclopentylmethyl-amide;
1-[5-(5-tert-Butyl-3-methanesulfonylamino-2-methoxy-phenylcarbamoyl)-2-methyl-phenyl]-1H-pyrazole-4-carboxylic acid (3-dimethylamino-2,2-dimethyl-propyl)-amide;
1-[5-(5-tert-Butyl-3-methanesulfonylamino-2-methoxy-phenylcarbamoyl)-2-methyl-phenyl]-1H-pyrazole-4-carboxylic acid (pyridin-3-ylmethyl)-amide;
1-[5-(5-tert-Butyl-3-methanesulfonylamino-2-methoxy-phenylcarbamoyl)-2-methyl-phenyl]-1H-imidazole-4-carboxylic acid (2,2-dimethyl-propyl)-amide;
1-[5-(5-tert-Butyl-3-methanesulfonylamino-2-methoxy-phenylcarbamoyl)-2-methyl-phenyl]-1H-imidazole-4-carboxylic acid ethyl ester;
1-[5-(5-tert-Butyl-3-methanesulfonylamino-2-methoxy-phenylcarbamoyl)-2-methyl-phenyl]-1H-imidazole-4-carboxylic acid ((R)-1-phenyl-ethyl)-amide;
1-[5-(5-tert-Butyl-3-methanesulfonylamino-2-methoxy-phenylcarbamoyl)-2-methyl-phenyl]-1H-imidazole-4-carboxylic acid ((S)-1-phenyl-ethyl)-amide;
1-[5-(5-tert-Butyl-3-methanesulfonylamino-2-methoxy-phenylcarbamoyl)-2-methyl-phenyl]-1H-imidazole-4-carboxylic acid (pyridin-3-ylmethyl)-amide;
1-[5-(5-tert-Butyl-3-methanesulfonylamino-2-methoxy-phenylcarbamoyl)-2-methyl-phenyl]-1H-imidazole-4-carboxylic acid (3-dimethylamino-2,2-dimethyl-propyl)-amide;
1-[5-(5-tert-Butyl-3-methanesulfonylamino-2-methyl-phenylcarbamoyl)-2-methyl-phenyl]-1H-imidazole-4-carboxylic acid (2,2-dimethyl-propyl)-amide;
1-{5-[3-Methanesulfonylamino-2-methoxy-5-(1-methyl-cyclopropyl)-phenylcarbamoyl]-2-methyl-phenyl}-1H-imidazole-4-carboxylic acid (2,2-dimethyl-propyl)-amide;
1-{5-[3-Methanesulfonylamino-2-methoxy-5-(1-methyl-cyclopropyl)-phenylcarbamoyl]-2-methyl-phenyl}-1H-pyrazole-4-carboxylic acid (2,2-dimethyl-propyl)-amide;
1-{5-[5-tert-Butyl-2-((R)-methanesulfinyl)-phenylcarbamoyl]-2-methyl-phenyl}-1H-imidazole-4-carboxylic acid (2,2-dimethyl-propyl)-amide;
1-{5-[5-tert-Butyl-2-((R)-methanesulfinyl)-phenylcarbamoyl]-2-methyl-phenyl}-1H-pyrazole-4-carboxylic acid (2,2-dimethyl-propyl)-amide;

1-{5-[5-tert-Butyl-2-((S)-methanesulfinyl)-phenylcarbamoyl]-2-methyl-phenyl}-1H-imidazole-4-carboxylic acid (2,2-dimethyl-propyl)-amide;

1-{5-[5-tert-Butyl-2-((S)-methanesulfinyl)-phenylcarbamoyl]-2-methyl-phenyl}-1H-pyrazole-4-carboxylic acid (2,2-dimethyl-propyl)-amide and 5-Amino-1-[5-(5-tert-butyl-3-methanesulfonylamino-2-methoxy-phenylcarbamoyl)-2methyl-phenyl]-1H-pyrazole-3-carboxylic acid ethyl ester or the pharmaceutically acceptable salts thereof.

10. A pharmaceutical composition containing a pharmaceutically effective amount of a compound according to claim 1 and one or more pharmaceutically acceptable carriers and/or adjuvants.

11. A method of treating a disease or condition chosen from osteoarthritis, Crohn's disease and rheumatoid arthritis, said method comprising administering to a patient a pharmaceutically effective amount of a compound according to claim 1.

* * * * *